(12) United States Patent
Brennan et al.

(10) Patent No.: US 8,914,098 B2
(45) Date of Patent: Dec. 16, 2014

(54) MEDICAL AND VETERINARY IMAGING AND DIAGNOSTIC PROCEDURES UTILIZING OPTICAL PROBE SYSTEMS

(75) Inventors: Jeffrey Brennan, Los Angeles, CA (US); Mark Humayun, Glendale, CA (US); Sean Caffey, Manhattan Beach, CA (US)

(73) Assignee: oProbe, LLC, Pasadena, CA (US)

( * ) Notice: Subject to any disclaimer, the term of this patent is extended or adjusted under 35 U.S.C. 154(b) by 650 days.

(21) Appl. No.: 12/718,266

(22) Filed: Mar. 5, 2010

(65) Prior Publication Data

US 2010/0228124 A1  Sep. 9, 2010

Related U.S. Application Data

(60) Provisional application No. 61/158,362, filed on Mar. 8, 2009, provisional application No. 61/253,338, filed on Oct. 20, 2009, provisional application No. 61/265,505, filed on Dec. 1, 2009.

(51) Int. Cl.
| | |
|---|---|
| *A61B 6/00* | (2006.01) |
| *A61B 5/00* | (2006.01) |
| *A61M 25/01* | (2006.01) |
| *A61B 8/08* | (2006.01) |
| *A61B 17/00* | (2006.01) |
| *A61B 19/00* | (2006.01) |
| *A61B 8/12* | (2006.01) |
| *A61B 18/20* | (2006.01) |
| *A61N 5/00* | (2006.01) |

(52) U.S. Cl.
CPC .............. *A61M 25/01* (2013.01); *A61B 5/6852* (2013.01); *A61B 2017/00694* (2013.01); *A61B 2019/5234* (2013.01); *A61B 5/418* (2013.01); *A61B 2019/461* (2013.01); *A61B 8/12* (2013.01); *A61B 2019/5454* (2013.01); *A61B 5/415* (2013.01); *A61M 2025/0166* (2013.01); *A61B 2019/5251* (2013.01); *A61B 5/0066* (2013.01); *A61B 2017/00207* (2013.01); *A61B 8/5276* (2013.01); *A61B 19/5244* (2013.01); *A61B 18/20* (2013.01); *A61B 2019/5248* (2013.01); *A61N 5/00* (2013.01)

USPC ............ 600/478; 600/476; 356/248; 356/479

(58) Field of Classification Search
USPC ........... 356/246–255, 479; 600/407, 476–480
See application file for complete search history.

(56) References Cited

U.S. PATENT DOCUMENTS

| 5,321,501 A | 6/1994 | Swanson et al. |
|---|---|---|
| 5,459,570 A | 10/1995 | Swanson et al. |

(Continued)

FOREIGN PATENT DOCUMENTS

| EP | 1839561 | 10/2007 |
|---|---|---|
| WO | WO-99/49780 | 10/1999 |

(Continued)

OTHER PUBLICATIONS

International Search Report and Written Opinion mailed Jul. 1, 2011 for International Application No. PCT/US2010/026293 (23 pages).

(Continued)

*Primary Examiner* — Mark Remaly
(74) *Attorney, Agent, or Firm* — Bingham McCutchen LLP

(57) ABSTRACT

An imaging method includes providing a handpiece having a probe tip insertable into human or animal tissue disposed at an end thereof, and, an optical coherence tomography (OCT) probe connected to the handpiece such that a functionality of the OCT probe is provided at the probe tip. The probe tip is disposed adjacent to or into human or animal tissue. Imaging of the tissue, measuring at least one of a feature size or a quantifiable characteristic of a structure in the tissue for biometry analysis, and/or performing a diagnostic procedure on the tissue or a device implanted in the tissue is performed with the OCT probe.

15 Claims, 19 Drawing Sheets

(56) References Cited

U.S. PATENT DOCUMENTS

| | | | |
|---|---|---|---|
| 5,465,147 A | 11/1995 | Swanson | |
| 5,748,598 A | 5/1998 | Swanson et al. | |
| 5,784,352 A | 7/1998 | Swanson et al. | |
| 5,962,852 A | 10/1999 | Knuettel et al. | |
| 6,134,003 A | 10/2000 | Tearney et al. | |
| 6,160,826 A | 12/2000 | Swanson et al. | |
| 6,421,164 B2 | 7/2002 | Tearney et al. | |
| 6,485,413 B1 * | 11/2002 | Boppart et al. | 600/160 |
| 6,498,948 B1 | 12/2002 | Ozawa et al. | |
| 6,501,551 B1 | 12/2002 | Tearney et al. | |
| 6,564,087 B1 | 5/2003 | Pitris et al. | |
| 7,261,687 B2 | 8/2007 | Yang | |
| 7,364,543 B2 | 4/2008 | Yang et al. | |
| 2002/0166946 A1 | 11/2002 | Iizuka et al. | |
| 2006/0103850 A1 | 5/2006 | Alphonse et al. | |
| 2006/0132790 A1 | 6/2006 | Gutin | |
| 2006/0142657 A1 | 6/2006 | Quaid et al. | |
| 2006/0293563 A1 | 12/2006 | Banik et al. | |
| 2007/0038119 A1 | 2/2007 | Chen et al. | |
| 2007/0167678 A1 | 7/2007 | Moskowitz et al. | |
| 2007/0278389 A1 | 12/2007 | Ajgaonkar et al. | |
| 2008/0051629 A1 | 2/2008 | Sugiyama et al. | |
| 2008/0146941 A1 | 6/2008 | Dala-Krishna | |
| 2008/0181358 A1 | 7/2008 | Van Kampen et al. | |
| 2010/0041986 A1 | 2/2010 | Nguyen et al. | |
| 2010/0228119 A1 | 9/2010 | Brennan et al. | |
| 2010/0228123 A1 | 9/2010 | Brennan et al. | |
| 2010/0228132 A1 | 9/2010 | Brennan et al. | |
| 2010/0228238 A1 | 9/2010 | Brennan et al. | |

FOREIGN PATENT DOCUMENTS

| | | |
|---|---|---|
| WO | WO-00/42906 | 7/2000 |
| WO | WO-2006/054975 | 5/2006 |
| WO | WO-2007/038682 | 4/2007 |
| WO | WO-2007103721 | 9/2007 |
| WO | WO-2008/153999 | 12/2008 |
| WO | WO-2010/104752 | 9/2010 |

OTHER PUBLICATIONS

Invitation to Pay Additional Fees and Partial Search Report issued Nov. 22, 2010 for International Application No. PCT/US2010/026293 (6 pages).

International Preliminary Report on Patentability mailed Sep. 22, 2011 for International Application No. PCT/US2010/026293 (16 pages).

Invitation to Pay Additional Fees and Partial Search Report mailed Oct. 5, 2011 for International Application No. PCT/US2011/036195 (5 pages).

International Search Report and Written Opinion mailed Dec. 20, 2011 for International Application No. PCT/US2011/036196 (14 pages).

* cited by examiner

MEDICAL AND VETERINARY IMAGING AND DIAGNOSTIC PROCEDURES UTILIZING OPTICAL PROBE SYSTEMS

CROSS-REFERENCE TO RELATED APPLICATIONS

This application claims priority to and the benefit of, and incorporates herein by reference in their entireties, U.S. Provisional Patent Application No. 61/158,362, which was filed on Mar. 8, 2009, U.S. Provisional Patent Application No. 61/253,338, which was filed on Oct. 20, 2009, and U.S. Provisional Patent Application No. 61/265,505, which was filed on Dec. 1, 2009.

TECHNICAL FIELD

In various embodiments, the present invention relates generally to optical probes, and more specifically to optical probes with multiple diagnostic and/or therapeutic functions used in medical and veterinary applications. Further, embodiments of the present invention relate to imaging and diagnostic methods performed with such probes.

BACKGROUND

Advances in minimally invasive surgical procedures and the development of novel surgical instruments have enabled surgeons to access delicate areas of the body that were previously off-limits or only accessible through highly invasive procedures. These innovations have undoubtedly resulted in significant improvements in treatment options and patient outcomes for a variety of maladies. As the complexity of surgical procedures and the number of tools to diagnose and treat the underlying condition expand, surgeons are confronted with a variety of options. For example, retinal surgical procedures (which typically rely on a variety of instruments, including an illuminating light source, a treatment laser, a vitrector, an aspirator, etc.) are performed via ports or cannulated incisions in the eye, limiting the number of instruments that can be introduced into the eye simultaneously. Likewise, orthopedic procedures (e.g., knee reconstruction) typically involve a variety of instruments and tools, of which only a limited number can be inserted into the patient for access to the surgical site at any particular moment. The need to constantly swap out instruments because of limited access to the surgical site is frequently a problematic and time-consuming distraction to the surgeon.

In addition, new diagnostic techniques—including new or improved imaging modalities—provide surgeons with more information and a better understanding of the area being treated. This enables surgeon to collect, for example, real-time and non-destructive biopsies including analysis of regions that are typically difficult to access. These innovations have resulted in significant improvements in treatment options and patient outcomes for a variety of maladies. One such useful diagnostic technique is optical coherence tomography (OCT), an interferometric technique for noninvasive diagnosis and imaging utilizing (typically infrared) light. A particular mode of OCT, termed "A-scan," provides one-dimensional axial depth scans of the tissue of interest, thus providing information on the identity, size, and depth of subsurface features. A series of spatially adjacent A-scans (typically lying in a straight line) may be combined to form a two-dimensional reconstructed image of the imaged area (termed a "B-scan"), offering surgeons a visual reconstruction of subsurface features. Likewise, three-dimensional images, termed "C-scans," may be formed by "stacking" multiple B-scans.

Consequently, there is a continuing need to facilitate the use of surgical instruments and surgical devices that incorporate multiple functions (including new diagnostic techniques), thereby reducing difficulties associated with limited access to the surgical site in minimally invasive surgeries. Furthermore, there is a need for the development of new diagnostic and imaging procedures performed with such devices, such as optical probes, that enable fast and less invasive diagnosis of a variety of maladies and measurement of various human and animal tissues.

SUMMARY

Embodiments of the present invention include diagnostic, imaging, and measurement techniques utilizing devices such as optical probes. Such devices may incorporate several functional elements intended for diagnostic and therapeutic use during, e.g., surgical procedures. Specifically, devices in accordance with embodiments of the invention incorporate one or more of the following: a fiber-coupled optical assembly for OCT, a fiber-coupled endoillumination device, a fiber-coupled laser for therapeutic applications including but not limited to photocoagulation and tissue ablation, an ultrasound imaging probe, an electrocautery probe, an RF ablation probe, a cryosurgical probe, an irrigator, and a mechanical probe (e.g., for manipulating or cutting tissue).

Embodiments of the present invention also incorporate an OCT system and handheld probe with imaging and biometry measurement capabilities. In some implementations, an OCT imaging system incorporates a console and a probe capable of A-scan, B-scan, and C-scan imaging. The console has an optical system that includes an interferometer and an electronic processing back-end (e.g., a computer with data-acquisition hardware). The interferometer and associated optical elements in the console interface functionally with the probe, which serves as the sample arm for the interferometer.

Herein, the term "probe" refers to functionality rather than to necessarily a distinct physical apparatus. Accordingly, probes or probe functions may be implemented in individual, dedicated apparatus, or in a single physical structure providing the different functions. Probes may each be driven or controlled by a single driver, or instead, multiple (or even all) probes may be controlled by a single driver selectably actuable to provide the various functions.

In an aspect, embodiments of the invention feature an imaging method. A handpiece having (a) a probe tip insertable into human or animal tissue and disposed at an end thereof, and (b) an optical coherence tomography (OCT) probe connected thereto is provided. The functionality of the OCT probe is provided at the probe tip. The probe tip is disposed adjacent to or into human or animal tissue. Then, (i) imaging of the tissue, (ii) measuring a feature size and/or a quantifiable characteristic of a structure in the tissue for biometry analysis, and/or (iii) performing a diagnostic procedure on the tissue or a device implanted in the tissue is performed with the OCT probe.

The probe tip may be disposed into the tissue via a cannulated incision, an open incision, or an orifice. A second probe may be connected to the handpiece such that the functionality of the second probe is provided at the probe tip. The second probe may be an endoillumination probe, a laser therapy probe, an ultrasound imaging probe, an electrocautery probe, an RF ablation probe, a cryosurgical probe, an irrigator, or a mechanical probe. A feature size and/or a quantifiable characteristic of a lens capsule and/or a retina may be performed with the OCT probe.

A diagnostic procedure may be performed with the OCT probe. The diagnostic procedure may include or consist essentially of monitoring the status of or quantifying quality of a treatment burn on a retina; monitoring the status of an ablative treatment on the tissue; quantifying the grade of chondromalacia in articular cartilage; identifying the presence and/or the location of subretinal fluid; delineating the margin of a tumor; measuring a corneal angle and/or a corneal thickness; measuring the thickness, integrity, or anatomical variation of a capsular bag; measuring the thickness of a retina; and/or measuring the thickness and/or density of articular cartilage.

In another aspect, embodiments of the invention feature a device including a handpiece having a probe tip at one end. Multiple probes are connected to the handpiece such that the functionality of each is provided at the probe tip. The probes may include or consist essentially of an optical coherence tomography (OCT) probe, an endoillumination probe, a laser therapy probe, an ultrasound imaging probe, an electrocautery probe, an RF ablation probe, a cryosurgical probe, an irrigator, and/or a mechanical probe. The probe tip may include or consist essentially of a rotatable outer needle, and, disposed at least partially within the outer needle, a rotatable inner needle. The probe tip may include a non-rotatable outer sleeve disposed around the outer needle. The probes may include or consist essentially of at least two of the OCT probe, the endoillumination probe, or the laser therapy probe.

Each of the probes may include or consist essentially of a physically and optically separate optical fiber, each of the optical fibers terminating at an output facet within the probe tip. The end of each of the optical fibers may include or consist essentially of means for coupling to a driver. A plurality of lenses may be disposed proximate the probe tip, and each of the lenses may have different refractive properties and may be optically connected to one of the optical fibers. At least one of the optical fibers may be slideably movable within the handpiece.

The probes may include or consist essentially of first, second, and third optical probes that include or consist essentially of first, second, and third optical fibers, respectively. The first and second optical fibers may be optically coupled into a fourth optical fiber, and the third and fourth optical fibers may each terminate at an output facet within the probe tip. The first and second optical fibers may be coupled into the fourth optical fiber via an optical combiner, a fused-fiber coupler, or a wavelength-division multiplexer. The first optical probe may include or consist essentially of an endoillumination probe, the second optical probe may include or consist essentially of a laser therapy probe, and the third optical probe may include or consist essentially of an OCT probe. The third optical fiber may include or consist essentially of a single-mode fiber and the fourth optical fiber may include or consist essentially of a multi-mode fiber. The first optical probe may include or consist essentially of an OCT probe, the second optical probe may include or consist essentially of a laser therapy probe, and the third optical probe may include or consist essentially of an endoillumination probe. The third optical fiber may include or consist essentially of a multi-mode fiber and the fourth optical fiber may include or consist essentially of a single-mode fiber. The first optical fiber may include or consist essentially of a tapered multi-mode optical fiber coupled to a white-light source. The white-light source may emit non-coherent light. A doped fiber and a laser light source may be coupled to the proximal end of the first optical fiber, and the doped fiber may emit white light when excited by the laser light source. Discrete sources of red, blue, and green light (each of which may include or consist essentially of a laser) may be coupled to the proximal end of the first optical fiber. The distal end of the first optical fiber may emit substantially white light. Each of the discrete sources of red, blue, and green light may be individually controllable, thereby controlling the wavelength of the light emitted from the distal end of the first optical fiber.

The probes may include or consist essentially of first, second, and third optical probes that include or consist essentially of first, second, and third optical fibers, respectively. The first, second, and third optical fibers may be optically coupled into a fourth optical fiber that terminates at an output facet within the probe tip. The first, second, and third optical fibers may be coupled into the fourth optical fiber via an optical combiner, a fused-fiber coupler, or a wavelength-division multiplexer. The first optical fiber may include or consist essentially of a tapered multi-mode optical fiber coupled to a white-light source. The white-light source may emit non-coherent light. A doped fiber and a laser light source may be coupled to the proximal end of the first optical fiber, and the doped fiber may emit white light when excited by the laser light source. Discrete sources of red, blue, and green light (each of which may include or consist essentially of a laser) may be coupled to the proximal end of the first optical fiber. The distal end of the first optical fiber may emit substantially white light. Each of the discrete sources of red, blue, and green light may be individually controllable, thereby controlling the wavelength of the light emitted from the distal end of the first optical fiber.

The probes may include or consist essentially of first and second optical probes that include or consist essentially of first and second optical fibers, respectively. The first and second optical fibers may be optically coupled into a third optical fiber that terminates at an output facet within the probe tip. The first and second optical fibers may be coupled into the third optical fiber via an optical combiner, a fused-fiber coupler, or a wavelength-division multiplexer. The first optical fiber may include or consist essentially of a tapered multi-mode optical fiber coupled to a white-light source. The white-light source may emit non-coherent light. A doped fiber and a laser light source may be coupled to the proximal end of the first optical fiber, and the doped fiber may emit white light when excited by the laser light source. Discrete sources of red, blue, and green light (each of which may include or consist essentially of a laser) may be coupled to the proximal end of the first optical fiber. The distal end of the first optical fiber may emit substantially white light. Each of the discrete sources of red, blue, and green light may be individually controllable, thereby controlling the wavelength of the light emitted from the distal end of the first optical fiber. The first, second, and third optical fibers may each consist essentially of or consist of a single-mode optical fiber. The first optical probe may be an OCT probe and the second probe may be an endoillumination probe or a laser therapy probe. The first optical fiber may consist essentially of or consist of a single-mode optical fiber, and the second and third optical fibers may each consist essentially of or consist of a multi-mode optical fiber.

The probes may include an OCT probe that includes or consists essentially of an optical fiber and an OCT lens assembly. The optical fiber may be coupled to the handpiece, and the OCT lens assembly may be disposed within the probe tip. The optical fiber may be coupled to the handpiece with a fiber-optic rotary joint. The optical fiber may be disposed within a stationary needle or sleeve coupled to the handpiece.

The probes may include an endoillumination probe that includes or consists essentially of an optical fiber for propagating light from a light source to the probe tip. The endoillumination probe may include a white light source that is at least partially disposed within the handpiece. The white light source may include or consist essentially of one or more light-emitting diodes.

The probes may include a laser therapy probe that includes or consists essentially of an optical fiber for propagating light from a narrow-wavelength light source to the probe tip. The laser therapy probe may be configured for photocoagulation and/or tissue ablation.

The functionality of each of the probes may be provided through a single optical fiber disposed within the probe tip. The functionalities may all be controlled by a single driver having selectable modes, each mode corresponding to one of the probes. The single optical fiber may include or consist essentially of multiple waveguides, each waveguide associated with at least one (or only one) probe. A separate lens (or separate portion of a single lens) disposed within the handpiece may be associated with each of the waveguides.

In a further aspect, embodiments of the invention feature a method of forming a device. A handpiece having a probe tip disposed at its end is provided, and multiple probes are connected to the handpiece such that a functionality of each is provided at the probe tip. The probes may include or consist essentially of an optical coherence tomography (OCT) probe, an endoillumination probe, a laser therapy probe, an ultrasound imaging probe, an electrocautery probe, an RF ablation probe, a cryosurgical probe, an irrigator, and/or a mechanical probe.

In yet another aspect, embodiments of the invention feature a device including or consisting essentially of a handpiece and a plurality of optical coherence tomography (OCT) probes connected to the handpiece. The handpiece has a probe tip disposed at one end, and a functionality of each of the probes is provided at the probe tip. Each of the OCT probes may include or consist essentially of a physically and optically separate optical fiber, each of the optical fibers terminating at an output facet within the probe tip. Each of the output facets may direct light therethrough in a different direction (e.g., perpendicular to another output facet). The functionality of each of the OCT probes may be provided through a single optical fiber disposed within the probe tip. The functionalities may all be controlled by a single driver having selectable modes, each mode corresponding to one of the probes. The single optical fiber may include or consist essentially of multiple waveguides, and each waveguide may transmit light corresponding to one of the OCT probes. Any or all of the OCT probes may have A-scan, B-scan, and/or C-scan functionality. An additional probe may be connected to the handpiece. The additional probe may be an endoillumination probe, a laser therapy probe, an ultrasound imaging probe, an electrocautery probe, an RF ablation probe, a cryosurgical probe, an irrigator, or a mechanical probe.

In a further aspect, embodiments of the invention feature a method of forming a device. A handpiece having a probe tip disposed at its end is provided, and multiple OCT probes are connected to the handpiece such that a functionality of each is provided at the probe tip.

In another aspect, embodiments of the invention feature a device including or consisting essentially of a handpiece and an optical coherence tomography (OCT) probe connected to the handpiece. The handpiece has a probe tip disposed at one end, and a functionality of the probe is provided at the probe tip. A sensor responsive to movement and/or handling of the handpiece for controlling the functionality of the OCT probe is disposed within or on the handpiece. The sensor may include or consist essentially of an accelerometer and/or a gyroscope, or may include or consist essentially of a touch sensor and/or a resistive sensor. The device may include circuitry for recognizing gestures associated with movement of the handpiece, the recognized gestures corresponding to commands relating to the functionality of the OCT probe, and/or recognizing patterns associated with handling of the handpiece, the recognized patterns corresponding to commands relating to the functionality of the OCT probe. A second probe may be connected to the handpiece. The second probe may be an endoillumination probe, a laser therapy probe, an ultrasound imaging probe, an electrocautery probe, an RF ablation probe, a cryosurgical probe, an irrigator, or a mechanical probe.

In yet another aspect, embodiments of the invention feature a device including or consisting essentially of a handpiece having a probe tip disposed at one end and being capable of performing multiple functions. The functions may include or consist essentially of optical coherence tomography (OCT), endoillumination, laser therapy, ultrasound imaging, electrocautery, RF ablation, cryosurgery, irrigation, and/or mechanical manipulation. A sensor responsive to movement and/or handling of the handpiece for controlling the functions of the probe is disposed within or on the handpiece. The sensor may include or consist essentially of an accelerometer and/or a gyroscope, or may include or consist essentially of a touch sensor and/or a resistive sensor. The device may include circuitry for recognizing gestures associated with movement of the handpiece, the recognized gestures corresponding to commands relating to the functions, and/or recognizing patterns associated with handling of the handpiece, the recognized patterns corresponding to commands relating to the functions.

In a further aspect, embodiments of the invention feature a system including or consisting essentially of a handpiece, an OCT probe connected to the handpiece, a camera for detecting movement and/or position of the probe tip, and circuitry for recognizing gestures associated with movement of the handpiece. The handpiece has a probe tip disposed at one end, and a functionality of the OCT probe is provided at the probe tip. The circuitry is operably connected to the OCT probe. At least one marker may be disposed on the handpiece, and the camera may detect the movement and/or position of the probe tip by detecting the marker(s). The marker(s) may include or consist essentially of at least one light-emitting diode. A second probe may be connected to the handpiece such that the functionality of the second probe is provided at the probe tip. The second probe may be an endoillumination probe, a laser therapy probe, an ultrasound imaging probe, an electrocautery probe, an RF ablation probe, a cryosurgical probe, an irrigator, or a mechanical probe.

In another aspect, embodiments of the invention feature a system, for use with a cannula insertable into human or animal tissue, for measuring relative motion during a surgical procedure. The system includes or consists essentially of a probe having a probe tip insertable into the cannula, as well as means for determining relative motion between the cannula and the probe tip. The motion-determining means may be contactless. The motion-determining means may include or consist essentially of at least one fiduciary marker on the cannula and/or the probe tip. The motion-determining means may include or consist essentially of a magnetic material and a magnetic sensor, one of which is disposed on the cannula and one of which is disposed on the probe tip. The magnetic sensor may include or consist essentially of a conductive coil. The motion-determining means may include or consist essentially of a photoreflective material and a photosensor, one of which is disposed on the cannula and one of which is disposed on the probe tip. The motion-determining means may include or consist essentially of an accelerometer and/or a gyroscope disposed on the probe tip.

In yet another aspect, embodiments of the invention feature a method for determining distance between a probe tip and tissue during a surgical procedure. A handpiece having (a) a probe tip insertable into human or animal tissue and disposed at an end thereof, and (b) an optical coherence tomography (OCT) probe connected thereto is provided. The functionality of the OCT probe is provided at the probe tip, and the OCT probe includes a probe lens. The probe tip is disposed adjacent to or into human or animal tissue. The distance between the probe tip and the tissue is determined by measuring the amount of reflected light captured by the probe lens. A second probe may be connected to the handpiece such that the functionality of the second probe is provided at the probe tip. The second probe may be an endoillumination probe, a laser therapy probe, an ultrasound imaging probe, an electrocautery probe, an RF ablation probe, a cryosurgical probe, an irrigator, or a mechanical probe.

In a further aspect, embodiments of the invention feature a method for determining distance between a probe tip and tissue during a surgical procedure. A handpiece having (a) a probe tip insertable into human or animal tissue and disposed at an end thereof, and (b) an optical coherence tomography (OCT) probe connected thereto is provided. The functionality of the OCT probe is provided at the probe tip, and the OCT probe includes a probe lens. The probe tip is disposed adjacent to or into human or animal tissue. An OCT reflectance profile of the tissue is measured with the OCT probe, and the distance between the probe tip and the tissue is determined from a reflection of the reflectance profile. A second probe may be connected to the handpiece such that the functionality of the second probe is provided at the probe tip. The second probe may be an endoillumination probe, a laser therapy probe, an ultrasound imaging probe, an electrocautery probe, an RF ablation probe, a cryosurgical probe, an irrigator, or a mechanical probe.

In yet another aspect, embodiments of the invention feature a method for modulating probe output. The tip of a probe is disposed proximate human or animal tissue, the distance between the tip and the tissue (or a feature within the tissue) is measured, and the output of the probe is modulated based on the measured distance. The probe may include OCT functionality available at the tip. The output may include or consist essentially of white light for endoillumination and/or laser light for laser therapy.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawing, in which.

DETAILED DESCRIPTION

Figure 1:
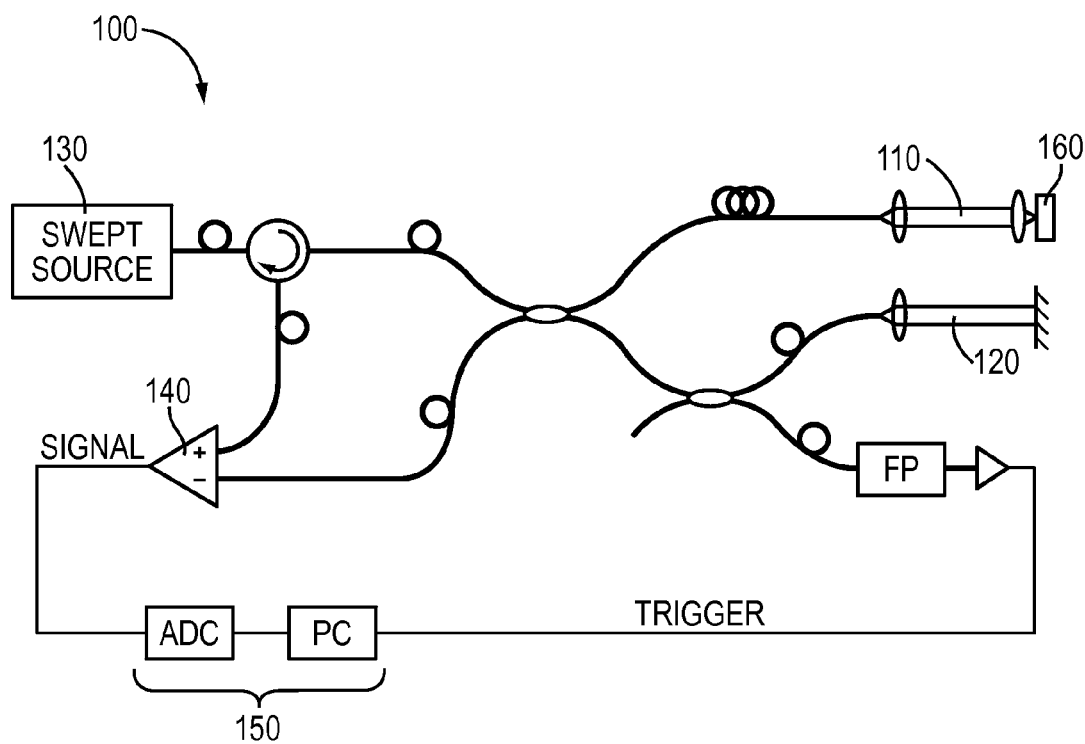
FIG. 1 is a schematic diagram of components of an OCT interferometry system in accordance with various embodiments of the invention.

FIG. 1 depicts an exemplary OCT interferometry system 100 in accordance with embodiments of the present invention, although alternative systems with similar functionality are also within the scope of the invention. As depicted, OCT interferometry system 100 includes a sample arm (or "probe") 110, a reference arm 120, a light source 130, a photodetector 140, and data-acquisition and processing hardware (or "driver") 150. Light from light source 130 travels through optical fibers to probe 110 and reference arm 120. Via probe 110, the light illuminates a sample 160, which may include or consist essentially of, e.g., biological tissue. Various features of interest of sample 160 reflect the light in different amounts or from different depths. The reflected light is combined with light reflected by reference arm 120 (which typically includes or consists essentially of a mirror), and the interference pattern thus generated provides information about the spatial dimensions and location of structures within sample 160. Light source 130 may be, e.g., a swept-source or tunable laser. Although only one light source is depicted in FIG. 1, various embodiments of the invention incorporate multiple light sources, as further described below. Such other light sources impart additional functionality to OCT interferometry system 100.

Hardware 150 may be a personal-computer-(PC-) based architecture, and may include a high-speed analog-to-digital converter (for example, on a PCI bus) that digitizes the output of photodetector 140 at a sampling rate ranging from several million samples per second to several billion samples per second. In an embodiment, the digitized data is processed by the PC processor and readily available or straightforwardly implemented software that, e.g., performs a Fourier transform and signal processing and reconstruction algorithms on the data. In another embodiment the data processing is performed in dedicated hardware, e.g., an ASIC, FPGA, DSP, or combination of these devices. The hardware and/or associated software derives, e.g., reconstructed images, biometric measurements, and/or quantitative data from the data produced by OCT interferometry system 100.

Figure 2A:
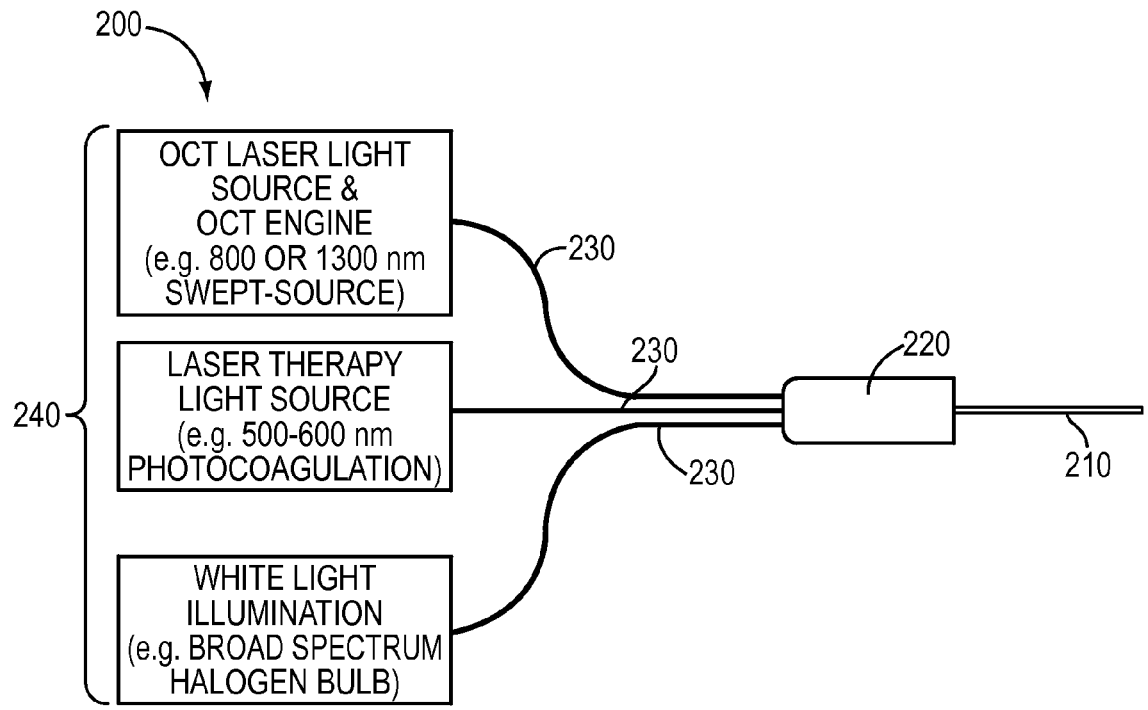
FIG. 2A is a schematic diagram of an OCT interferometry system incorporating light from multiple light sources in accordance with various embodiments of the invention.
Figure 2B:
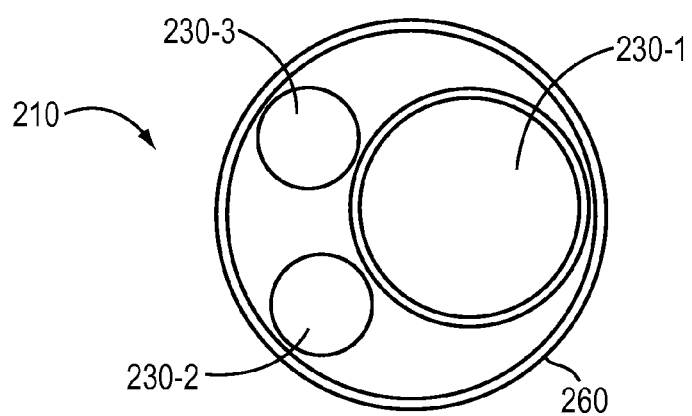
FIG. 2B is a cross-sectional diagram of the probe tip of the system depicted in FIG. 2A.

FIGS. 2A and 2B are, respectively, a simplified representation of an exemplary probe 200 for use with OCT interferometry system 100 and a cross-section of a tip 210 of probe 200. Probe 200 includes a handle 220 housing one or more independent optical fibers 230 that terminate within tip 210. The optical fibers 230 each transmit light from one of a variety of light sources 240, which may provide, e.g., endoillumination for visualization, OCT imaging and/or biometry for visualization and diagnosis, and/or photocoagulation or tissue ablation for therapeutic treatment. Tip 210 includes or consists essentially of a hollow needle having an outer sleeve 250, and houses the ends of optical fibers 230. In an exemplary embodiment, optical fiber 230-1 provides forward-scanning OCT functionality via light from a laser light source, optical fiber 230-2 provides therapeutic functionality via light from a laser light source, and optical fiber 230-3 provides illumination via light from, e.g., a broad-spectrum white light source (e.g., a halogen light). Each functionality of probe 200 may be controlled by a separate driver (e.g., similar to hardware 150 described above), or a single driver may control all of the functionalities. Such a single driver may have selectable modes, each corresponding to one of the functionalities, that it may switch among at the user's direction.

Figure 3:
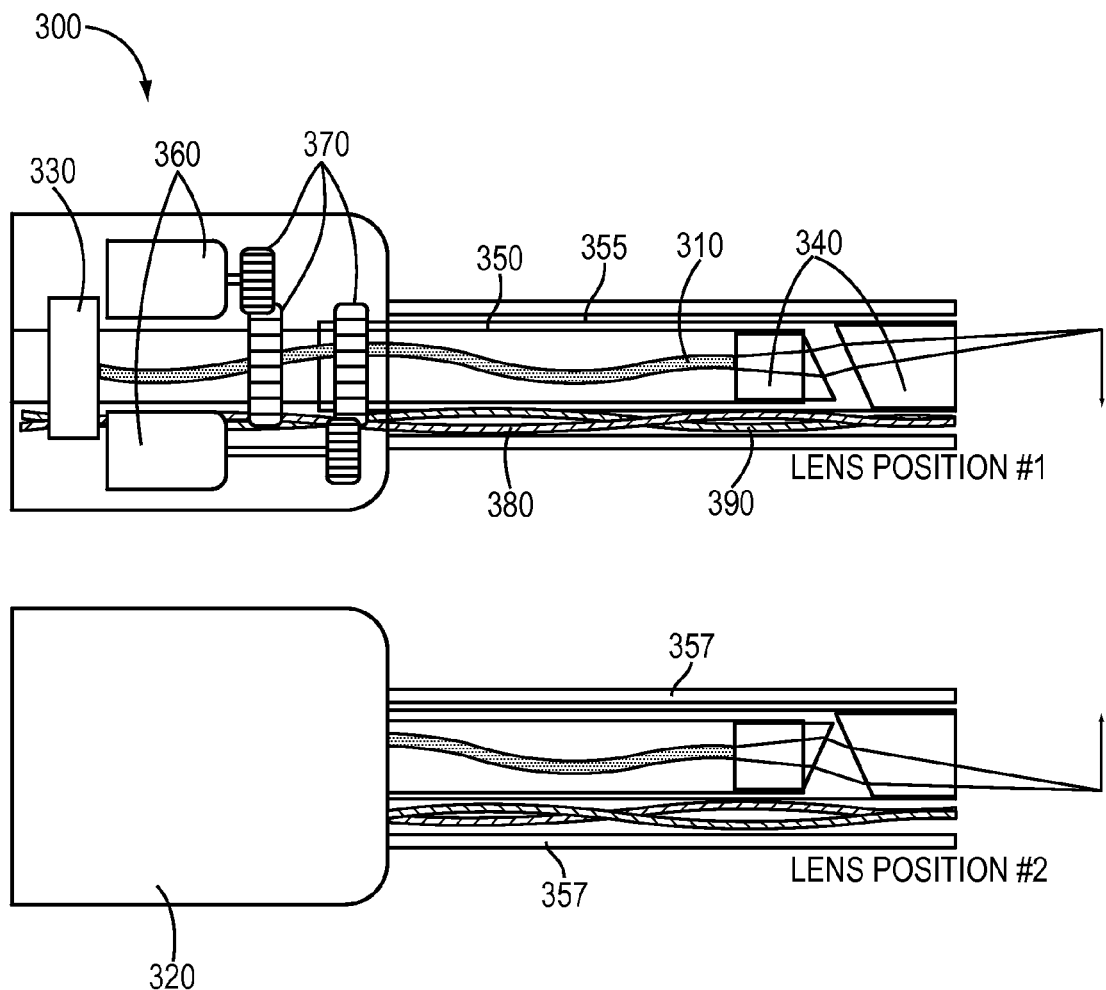
FIG. 3 depicts two schematic side views of a probe having optics positioned in different scanning positions in accordance with various embodiments of the invention.

In various embodiments of the present invention, probes incorporate forward-scanning OCT imaging functionality. FIG. 3 depicts two different internal OCT lens positions of a probe 300. Probe 300 includes an optical fiber 310 (which may be single-mode or multi-mode) that is coupled to a probe handpiece 320 via, for example, a fiber-optic rotary joint (FORJ) 330 that enables the OCT lens assembly to rotate freely. The OCT lens assembly includes or consists essentially of two counter-rotating lenses 340 mounted within two nested needles 350, 355 made from, for example, surgical-grade steel, polyimide, or polyether ether ketone (PEEK) hypodermic tubing. In an embodiment, needles 350, 355 are nested within an outer sleeve 357 (including or consisting essentially of, e.g., thin-walled polyimide tubing) that is secured to handpiece 320 such that outer sleeve 357 remains stationary while the nested needles 350, 355 are free to rotate therewithin. Outer sleeve 357 isolates and protects the surrounding environment (e.g., biological tissue, vitreous gel, etc.) from the movement of the rotating nested needles 350, 355.

Needles 350, 355 are mounted in handpiece 320 (e.g., an injection-molded ergonomic enclosure), which allows the needles to spin freely while securely held in place. In one embodiment, the lenses 340 are gradient-index (GRIN) lenses mounted in the tips of the nested needles 350, 355 and are either press-fit or secured with a biocompatible epoxy or other adhesive or sealant. A short length of fiber 310 within the inner needle 350 links the FORJ 330 with the first GRIN lens 340, and may be butt-coupled to the lens 340 and held in place with, e.g., a glass ferrule. Alternately, the fiber 310 may be fused to the lens 340 (e.g., via heat or chemical processes) or attached to the lens 340 via, e.g., epoxy. Optionally, index-matching gel may be applied at the interface between the fiber 310 and the lens 340, and/or anti-reflective (AR) coatings may be applied to the lenses 340. As shown in FIG. 3, the lenses 340 may be angled such that the light that emanates from the second GRIN lens 340 at the tip of probe 300 will scan, in an approximately linear motion, the region forward of the probe tip when the lenses 340 are counter-rotated at approximately the same speed (i.e., will scan from the position labeled "Lens Position #1" to the position labeled "Lens Position #2"). The rotation may be accomplished manually, by means of a collar arrangement, or via one or more motors 360 operating gears 370 or other power-coupling mechanism (e.g., a belt-drive mechanism and/or a friction-drive mechanism) operatively coupled to needles 350, 355. In an embodiment, motors 360 are replaced by a pneumatic or hydraulic system (preferably a closed system, such that little or no air or fluid is introduced into the imaging site) that produces rotation via, e.g., propellers mounted on needles 350, 355. The propellers rotate when exposed to an external air or fluid source that is connected to probe 300 via flexible tubing. In an embodiment, a thin spacer (e.g., an annular Teflon washer, not shown) is positioned between the two lenses 340 to reduce friction therebetween during lens rotation. As described above with reference to FIGS. 2A and 2B, probe 300 may also include fibers that provide additional functionality, e.g., treatment (or "therapeutic") fiber 380 and illumination fiber 390 (the functionalities of which are further described below). In an embodiment, each fiber within probe 300 terminates at a lens or lens array (like lenses 340) at the tip of probe 300. Each of these lenses may have different refractive properties, e.g., indices of refraction or shape (i.e., to direct and/or focus light therethrough).

Figure 4A:
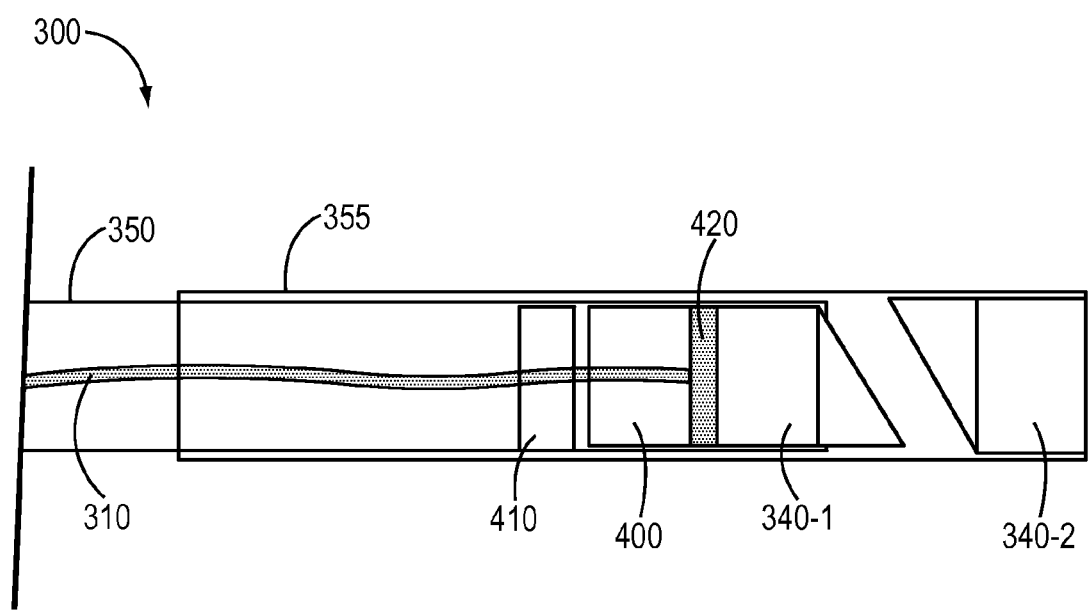
FIGS. 4A and 4B are schematic cross-sections of a probe having alternative means of joining a fiber to the probe tip assembly in accordance with various embodiments of the invention.

FIG. 4A depicts a simplified cross-sectional diagram of an embodiment of the tip of probe 300 utilizing an alternative approach to coupling fiber 310 to lens 340-1 within needles 350, 355. In this embodiment, FORJ 330 is replaced with a bushing 400 (which may be, e.g., a bearing, a bushing, or a sleeve such as stainless steel hypodermic or polyimide tubing) that may rotate freely within the inner needle assembly. A second bushing 410 is secured to the inner needle assembly to restrict the travel of fiber 310 along the longitudinal axis and to prevent fiber 310 from dislodging from the inner needle 350. The diameter of the inner hole in this "stop" bushing 410 is sufficiently large to allow fiber 310 to freely rotate therewithin. The distal end of fiber 310 is butt-coupled to the first GRIN lens 340-1 using, for example, a refractive index matching gel 420. Another embodiment of the invention eliminates both FORJ 330 and bushing 400 by keeping the internal needle 350 stationary and rotating only the outer needle 355, resulting in a circular (i.e., circumferential) scan pattern.

Figure 4B:
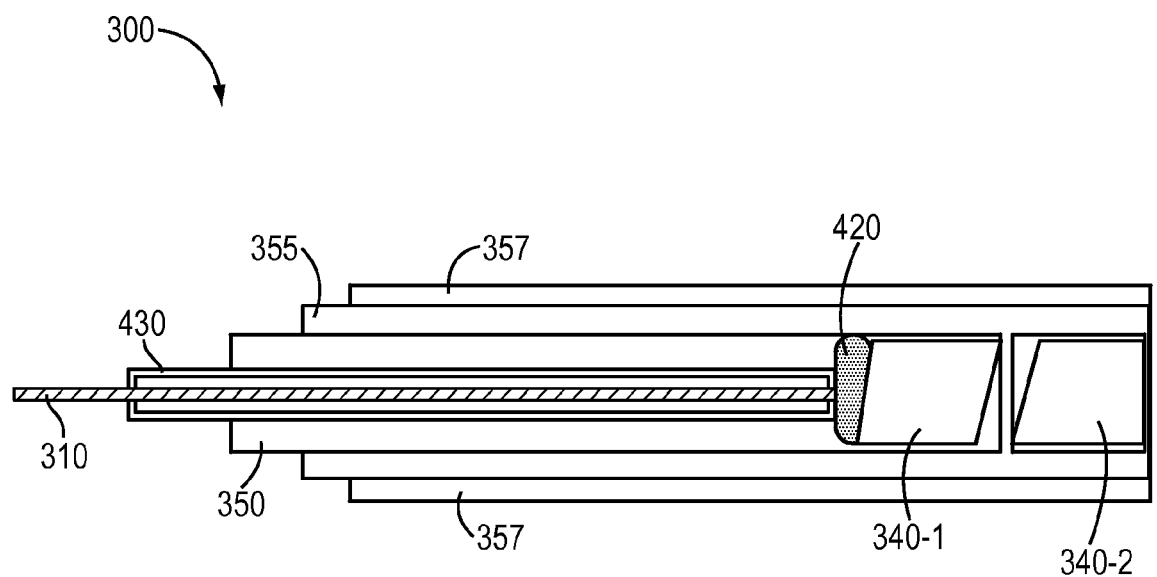

Another embodiment of the invention, depicted in FIG. 4B, replaces FORJ 330 with a stationary needle 430, which is nested within inner needle 350 and houses fiber 310. Stationary needle 430 is secured at the proximal end of the tip of probe 300 (at handpiece 320, not shown) to prevent rotation or movement. The distal end of fiber 310 is butt-coupled to lens 340-1 using, for example, refractive index matching gel 420. (FIG. 4B depicts inner needle 350, outer needle 355, stationary needle 430, fiber 310, and outer sleeve 357 as "unnested" at their proximal ends for ease of representation; in reality, these elements each extend to and/or through handpiece 320.)

Probe 300 enables a variety of scanning geometries that facilitate volumetric scans and other three-dimensional image reconstructions, as well as those optimized for biometry applications (e.g., measuring the angle of the ciliary body, length of lens capsule, and/or inflammatory state of a ciliary body), which may be achieved by varying the speed of each lens relative to the other. Referring back to FIG. 3, the two counter-rotating needles 350, 355 may be driven by a single motor 360 and couplings (gears 370 or other coupling). In another embodiment, the needles 350, 355 are driven by two motors 360, each of which may spin at a speed independent of the other. Different relative speeds may also be accomplished with a single motor 360 using different coupling (e.g., gear) ratios for each needle. In one embodiment, the gear ratios are selectable (e.g., through a mechanical lever) such that in one particular setting both needles 350, 355 counter-rotate at approximately the same speed (providing a linear scan), while in another setting needles 350, 355 rotate at different relative speeds to provide volumetric scans. Alternately, needles 350, 355 may be driven by a rotating cable drive (e.g., driven by a remote motor and torque transmission system) or a pneumatic or hydraulic system (e.g., driven by a remote pressurized air or fluid source, as described above) that is coupled to the probe handpiece 320.

Probe 300 optionally includes an on-board mechanism for measuring the angular velocity and/or position of one or both needles 350, 355, for example, a rotational sensor (not pictured) interfaced to analog or digital (e.g., a microcontroller) circuitry. Such a measurement mechanism determines the speed of the motor(s) 360 and may therefore be used to implement motor speed control via a feedback network (implemented, for example, in hardware 150). It may also facilitate determination of the orientation of the two lenses 340 relative to each other, the accuracy of which will typically be dictated by the resolution of the rotational sensing system. In general, a single linear scan of probe 300 consists of a multitude of "lines" or A-scans (for example, 512 A-scans per image frame), where a particular A-scan correlates to a specific position of the lenses 340 relative to each other. Incorporating a rotational sensor enables the processor to correlate sampled OCT data with a particular lens position and therefore a particular A-scan. The resolution of the scan may be improved by interpolation if the desired resolution exceeds the resolution of the sensor (e.g., 512 A-scans requires approximately 0.7 degree sensor resolution). The rotational sensor may include or consist essentially of, e.g., a set of mechanical contacts (or switches) that trigger upon a full revolution (or portion thereof) of inner needle 350, one or more magnetic (e.g., hall-effect) sensors that detect motion of a magnet on the rotating inner needle 350, and/or a rotary encoder.

In yet another embodiment, the rotational sensor incorporates an optical encoder, photoreflector, and/or photo-interrupter, which utilizes a small disk or wheel containing evenly spaced marks, notches, slots, or holes mounted orthogonally to needle 350, with needle 350 passing through the center of the disk. A light source (e.g., an LED) and a light sensor (e.g., a phototransistor) are mounted such that light from the light source reflects from the disk and is captured by the sensor; the darker regions reflect less light than the lighter regions, enabling determination of the rotation and position of the needle. Another embodiment accomplishes a similar effect utilizing a photo-interrupter, wherein the light source and sensor are located on opposite sides of the disk; as needle 350 rotates, the notched areas allow light to pass from the source to the sensor while the areas not containing notches block the light. In this manner the rotation and position(s) of the needle(s) may be measured. A simpler, lower-resolution embodiment detects needle rotation by sensing the reflection or lack of reflection of infrared light from the rotating needle itself. The reflectivity of the rotating needle may be adjusted by, for example, painting or laser-etching evenly spaced dark strips (resulting in more absorption and less reflection) and/or polishing adjacent areas to be more reflective.

With reference to FIGS. 2A and 3, fiber 310 emerges from the proximal end of the probe and couples to a light source (e.g., a laser) and a console that contains the required hardware for OCT image reconstruction. In a preferred embodiment, the OCT light source is a swept-source or tunable laser, and the OCT console includes or consists essentially of assorted optical components, an interferometer, a photodetector and sampling circuitry, and signal processing and computational capabilities for image reconstruction (as described above with reference to FIG. 1). Other OCT configurations that may be advantageously employed include the use of super-luminescent diode light sources as the OCT light source, and diffraction gratings and linear photodiode arrays may replace the photodetector. The engine may also include display and graphical user interface (GUI) capabilities for real-time or near real-time display of image reconstruction, as well as data storage capability.

In addition, due to the fact that the OCT light source typically operates in the non-visible infrared spectrum, some embodiments of the present invention include a mechanism for visualizing the location and scan path of the beam. An embodiment of the probe includes a visible laser light source (e.g., a 632 nm-wavelength laser) inserted into the light path through the use of an optical combiner or wavelength-division multiplexer (WDM). As the probe scans across a sample, the visible light beam translates with the OCT light beam, facilitating location of the beam's position.

As described above, in various embodiments probe 300 includes an endoillumination probe, which includes illumination fiber 390 (e.g., a single-mode or multiple-mode optical fiber) connected to a broad-spectrum light source (e.g., a halogen, mercury-vapor, or xenon broad-spectrum bulb). The light travels through fiber 390 and illuminates a region of interest of the sample. Depending on the specific application, the distal tip of fiber 390 may be terminated in any of a variety of ways. The tip of fiber 390 may simply be polished and/or angled to provide specific areas and angles of illumination, or may couple to one or multiple lenses, e.g., for the purpose of focusing the light or causing it to diverge. In an alternate configuration, a lens is integrated into fiber 390 via gradient indexing, where the index of refraction of the fiber itself is gradually varied across the longitudinal axis of fiber 390 to provide convergence or divergence of the propagating light. Using a lens to disperse the light enables the use of a smaller-diameter fiber 390 to achieve a similar area of illumination (spot size) at a given working distance, which is particularly useful in a multi-function probe in which multiple fibers are bundled together in close proximity.

In various embodiments, probe 300 incorporates functionality for thermal, photochemical, and/or photomechanical laser therapy treatment via treatment fiber 380. Fiber 380 (e.g., a single-mode or multi-mode optical fiber) propagates light from a narrow-wavelength light source (e.g., a laser or super-luminescent diode) to tissue (or other sample) for therapeutic treatment purposes, such as photocoagulation or tissue ablation. The wavelength of the light source may be chosen based on the application; for example, photocoagulation and many tissue ablation procedures typically use 532 nm-wavelength light due to selective absorption by hemoglobin. It should be noted that any of a variety of wavelengths may be selected depending on the procedure. In another embodiment of the invention, only two of the aforementioned functional elements (e.g., OCT imaging and endoillumination, or alternately OCT imaging and laser therapy) are implemented in probe 300.

In another embodiment of the invention, two or more of the optical fibers (e.g., fibers 230 in FIG. 2A) are optically coupled into a single optical fiber within or before reaching the handle of the probe. For example, the optical coupling may be accomplished via use of an optical combiner, a fused-fiber coupler, a wavelength-division multiplexer that propagates all wavelengths simultaneously along the fiber, or optical switches that switch between different light sources (e.g., of a light source that integrates both laser and broad-spectrum light sources). In an exemplary embodiment, the output of a laser therapy source and the output of a broad white-light spectrum (illumination) source are coupled into a single fiber, and only two fibers are required for OCT imaging, endoillumination, and laser therapy—i.e., light from the endoillumination and laser therapy light sources propagate through the same optical fiber and may be simultaneously activated or switched from one function to the other. Another variation combines laser therapy and OCT functions in a single fiber and uses a second fiber for white-light endoillumination. In these embodiments, the fiber utilized for OCT may be a single-mode fiber in order to reduce or eliminate modal dispersion of the OCT light, and the fiber utilized for endoillumination is a multimode fiber, as multimode fibers generally have larger cores and thus facilitate light coupling therewithin. In yet another embodiment, more than two functionalities, e.g., endoillumination, OCT, and laser therapy are combined into a single fiber via the above-described optical coupling techniques.

In preferred embodiments of the invention, the fiber providing OCT functionality in the probe is a single-mode fiber, thus eliminating modal dispersion in the fiber. The OCT light source may be coherent (e.g., a laser) or non-coherent (e.g., one or more light-emitting diodes (LEDs) or bulbs), and may be coupled to the fiber in any of several ways. The inherent difficulty in coupling light from a non-coherent source with a large radiating output pattern (e.g., LED or bulb) into a single-mode fiber generally limits the power-coupling efficiency and overall effectiveness of traditional optics solutions. One solution to this limitation combines a high-intensity non-coherent light source with an optical system including or consisting essentially of a series of lenses designed to successively focus the output of the light source into a spot size suitable for coupling to a single-mode fiber. Limitations in the optics and physical constraints generally limit the practical spot size and coupling efficiency that may be achieved in this manner.

Figure 5:
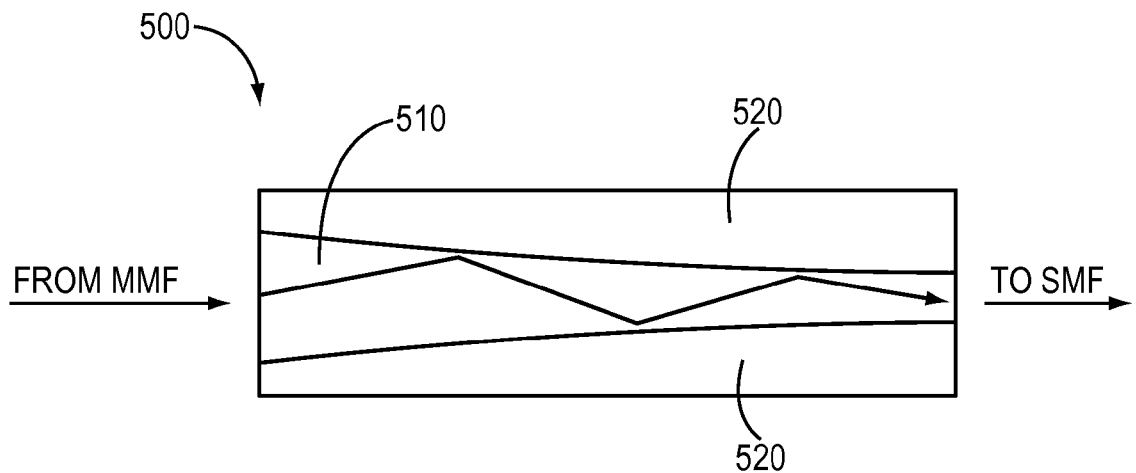
FIG. 5 is a schematic cross-section of a tapered optical fiber used with probe systems in accordance with various embodiments of the invention.

A preferred embodiment utilizes a single- or multiple-tapered multimode fiber to couple the light source to the single-mode fiber. FIG. 5 depicts a tapered fiber 500, in which the diameter of a core 510 is gradually tapered from a larger end (operatively coupled to the light source) to a smaller end (operatively coupled to the single-mode fiber carrying the light to the probe tip). The core 510 is surrounded by cladding 520, which is may also be tapered, thus providing tapered fiber 500 with a substantially unitary outer diameter. Additionally, lensing elements (e.g., graded-index lensing) or gradient-index fiber may be incorporated in various embodiments to focus the light and further reduce the beam spot size.

Embodiments of the invention feature any of a variety of methods of producing white light for endoillumination. Such methods include the use of non-coherent sources with sufficient power output for the intended application. These include, e.g., mercury-vapor and halogen lamps, which offer continuous visible spectra but may necessitate bulky optics, large components, higher current requirements, and the resultant heat generation. These sources may also be difficult to couple into small-diameter (e.g., single-mode) fibers without significant power-coupling losses. High-intensity LEDs may also be utilized. White light may be produced from LEDs via the mixing of different visible wavelengths (e.g., red, green, and blue), which produces a non-continuous spectrum, or via the excitation of a phosphor using an LED of a specific wavelength (typically in the ultraviolet range). In addition, the small size of LEDs allows their direct integration into the probe handpiece. Like the aforementioned light sources, LEDs are readily coupled to multimode fibers but may suffer from significant power-coupling losses when coupled to single-mode fibers. Finally, white-light endoillumination may be provided using coherent sources (e.g., lasers). In an embodiment, the white-light output is obtained by mixing multiple wavelengths from different laser sources (e.g., red, green, and blue), similar to the above description for LEDs. Specially doped fiber that produces white light by fluorescing or creating stimulated emission at specific wavelengths when excited by a laser source may also be used. This can be accomplished, for example, using multi-clad fiber wherein the excitation or lasing source is propagated in the intermediate cladding and the doped region is concentrated in the fiber core.

Figure 6A:
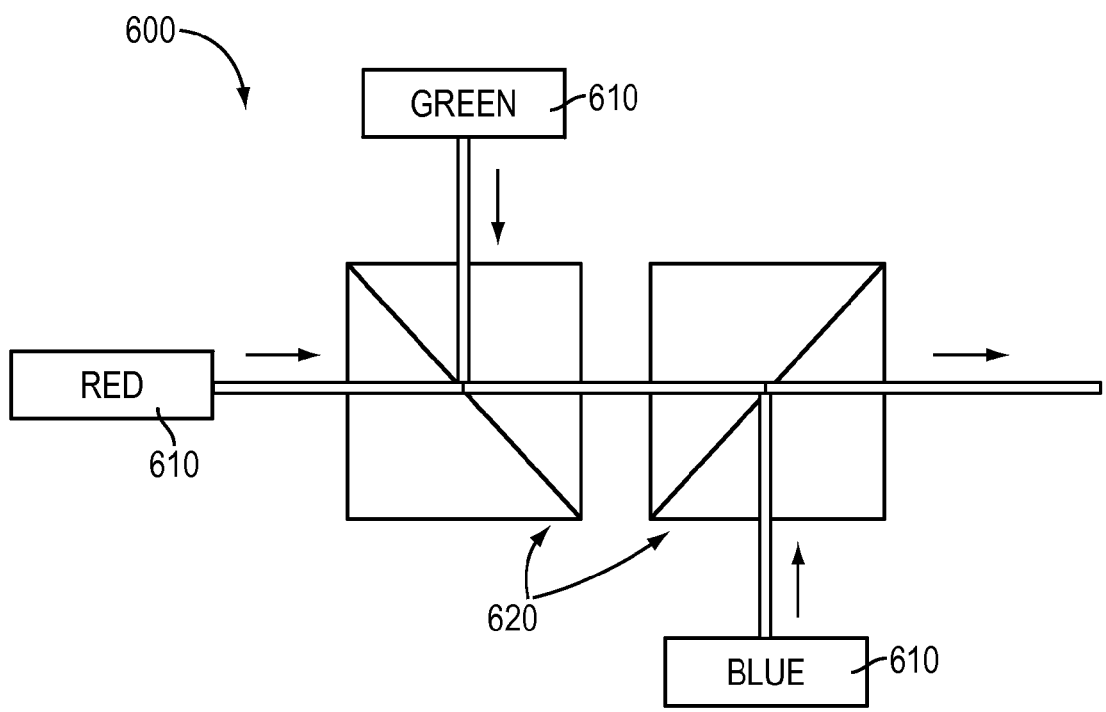
FIGS. 6A and 6B are schematic diagrams of white-light sources formed via color-mixing of multiple input light sources in accordance with various embodiments of the invention.
Figure 6B:
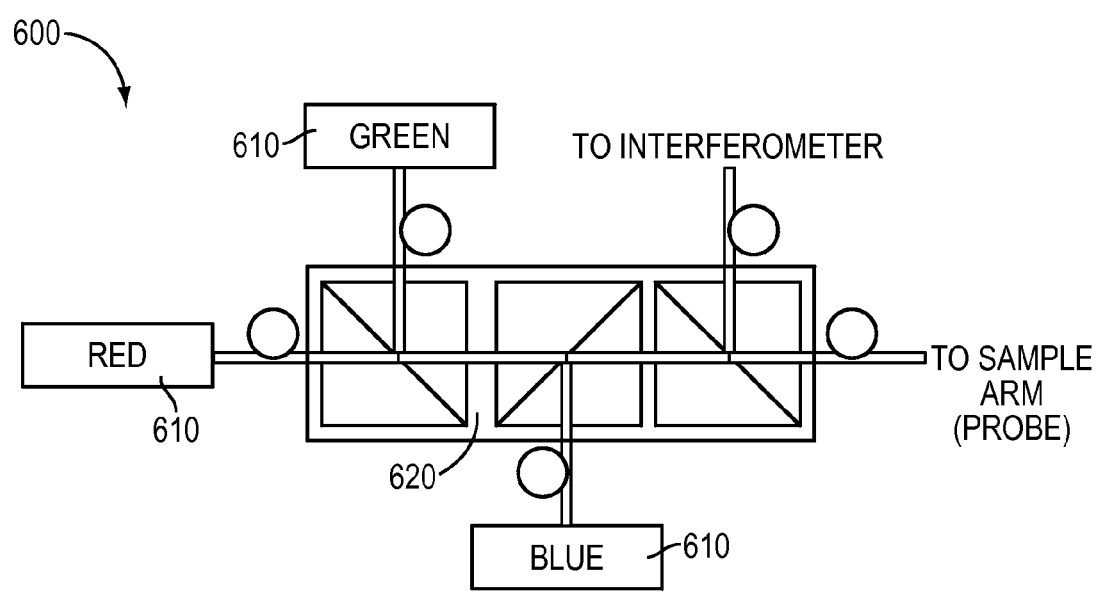

Referring to FIG. 6A, in some embodiments, the probe system utilizes a white-light laser system 600 that operates by mixing the light output of multiple constituent lasers 610 with different wavelengths, e.g. in the red, green, and blue range. The constituent lasers 610 may be fiber-coupled lasers (as shown in FIG. 6B). As shown, the light of the constituent lasers 610 is combined by an optical combiner 620 (e.g., a wavelength-division multiplexer). In a preferred embodiment shown in FIG. 6B, optical combiner 620 combines the light from the three depicted constituent lasers 610 (e.g., red, green, and blue light, collectively "RGB") with the fiber-coupled light path to the sample arm of the OCT system (e.g., as shown in FIG. 1) into a single fiber-coupled output suitable for interface to the handheld probe using single-mode fiber. There is typically no need for an additional aiming beam (e.g., of red light, as described above) when using white-light laser system 600, because it is straightforward to disable one or more of constituent lasers 610, resulting in output light of a selected color (e.g., red) that may be used for aiming purposes. White-light laser system 600 may also produce light of multiple colors by mixing the amount of red, green, and blue light. The intensity of each wavelength may be varied in order to alter their respective contributions to the endoillumination light output, e.g., to provide different therapeutic effects, provide improved visualization, or prevent tissue damage. This may enable a surgeon to view tissue under different hues of white light, which is useful in accentuating certain features, e.g., improving the contrast of certain structures (e.g., blood vessels) or stains, and/or causing stains to fluoresce (e.g., ophthalmic use of indocyanine green or tryptan blue). Likewise, the intensity of contributing wavelengths may be adjusted to comply with safety guidelines such as those recommended by the International Commission on Non-Ionizing Radiation Protection to, for example, prevent photochemical retinal damage. In one embodiment, the intensity of the blue contribution may be lowered in order to limit the blue spectral light from a white-light laser system 600. For example, light having wavelengths lower than approximately 475 nm may be filtered out of the output of white-light laser system 600 in order to protect against phototoxicity. Such selected wavelengths may also be filtered out with an external filter coupled to white-light laser system 600 or probe 300.

Figure 7:
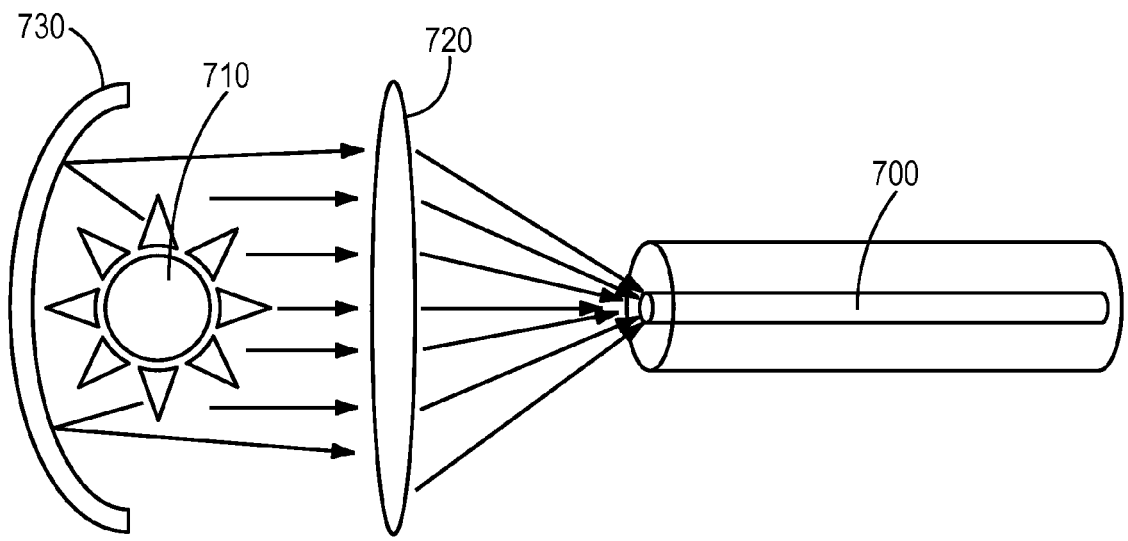
FIG. 7 is a schematic diagram of a method of coupling light into an optical fiber in accordance with various embodiments of the invention.

Referring to FIG. 7, in many embodiments, a multi-mode fiber 700 is the preferred optical propagation medium for endoillumination because the larger diameter core of the multi-mode fiber (e.g., a core diameter ranging from approximately 50 μm to approximately 1000 μm) facilitates coupling and propagation of high-power light. However, a solution based solely on multi-mode fibers may diminish OCT system performance (e.g., resolution) due to modal dispersion. The multi-mode fiber 700 couples light from a coherent (e.g., laser) or non-coherent (e.g., LED or mercury-vapor bulb) light source 710. A single or multi-lens system 720 may be used to collimate and/or focus the light emanating from the light source 710, which is typically located at or near the focal length of a reflector 730, into the core of multi-mode fiber 700 with the coupling efficiency improving as the diameter of its core increases. Alternatively, a fiber-coupled light source (e.g., white-light laser system 600) may be used and may be directly attached (e.g., via a FC/PC connector) to the multi-mode fiber 700.

The multi-mode fiber 700 may be combined with the OCT light path via a wavelength-division multiplexer, with the OCT sample arm at the output. In various embodiments, it is desirable to balance the diameter of multi-mode fiber 700 with the desired OCT resolution. For example, depending on the application, the degraded performance due to modal dispersion in 50-μm core diameter multi-mode fiber 700 may be acceptable whereas the degradation resulting from a 200-μm core diameter may not be.

Figure 8:
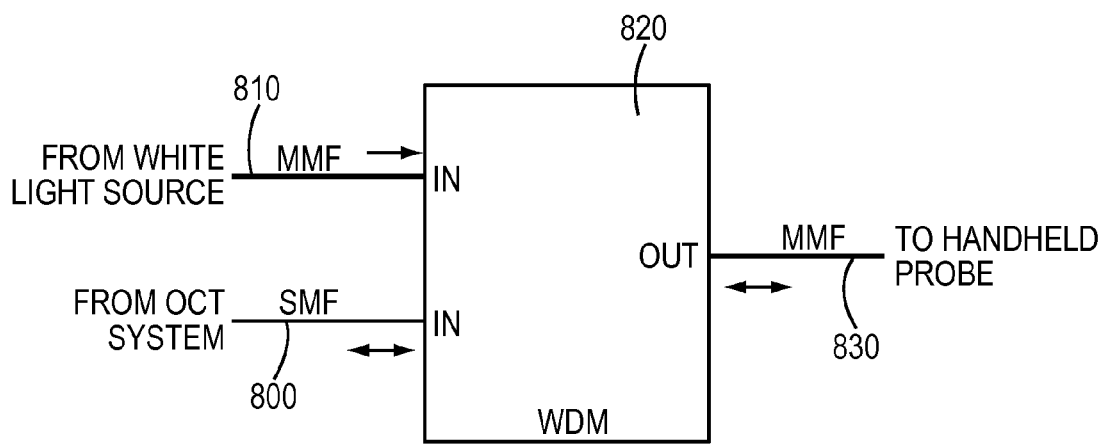
FIG. 8 is a schematic diagram of an optical fiber coupling apparatus in accordance with various embodiments of the invention.

Another embodiment of the invention, illustrated in FIG. 8, incorporates both single-mode and multi-mode fiber in different branches of the optical system to exploit the benefits and minimize the detriments of each. In this embodiment, a single-mode fiber 800 propagates light from the OCT system with substantially no modal dispersion, and a multi-mode fiber 810 propagates white light for endoillumination. A bidirectional WDM 820 couples the light from single-mode fiber 800 and multi-mode fiber 810 and outputs both into a multi-mode fiber 830, which is connected to the handpiece of the probe. Thus, high-power endoillumination and low-dispersion OCT are enabled in the same system. Modal dispersion in the OCT system is minimized, as the OCT light travels primarily through single-mode fiber and propagates through multi-mode fiber only in the probe handpiece (or a short distance leading thereto). WDM 820 typically contains a single-mode to multi-mode converter to minimize coupling loss.

Figure 9:
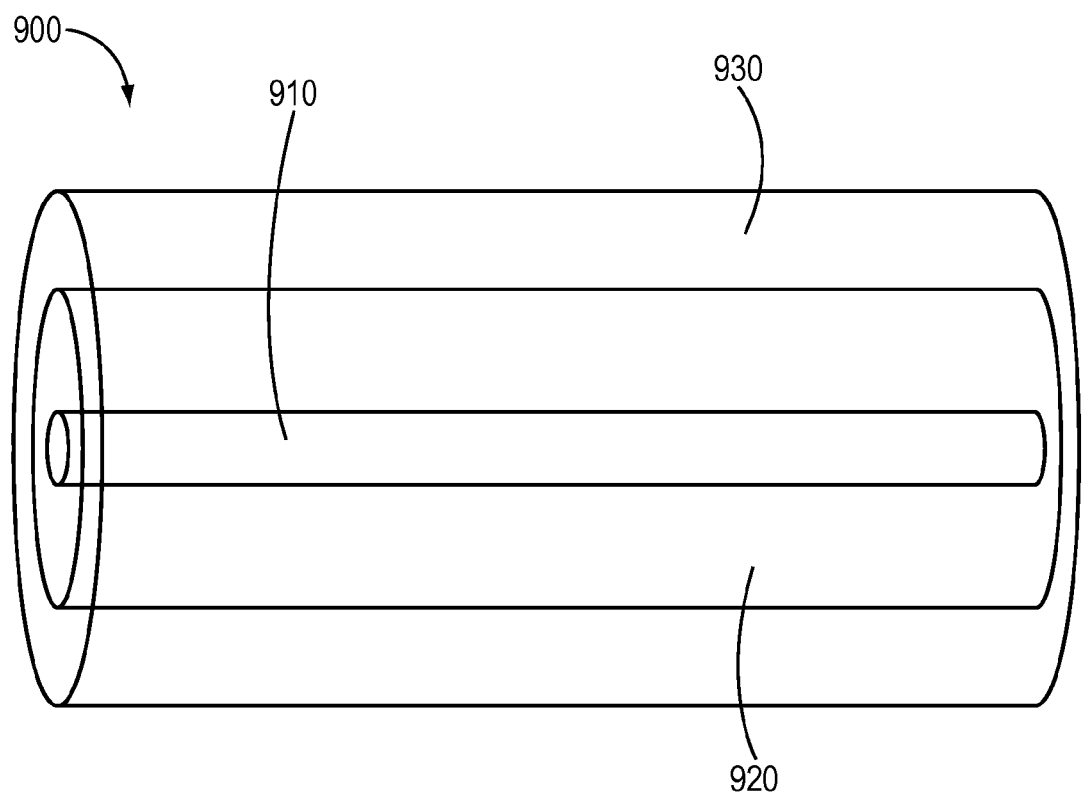
FIG. 9 is a schematic diagram of a multiple-clad optical fiber in accordance with various embodiments of the invention.

As shown in FIG. 9, light for endoillumination and OCT may even share a single fiber in probes according to some embodiments of the invention. A double-clad fiber 900 includes an inner core 910, an intermediate cladding 920, and an outer cladding 930. An outer coating or jacket (shown in FIG. 11C) surrounding the outer cladding 930 may be used as a protective layer. Typically both intermediate cladding 920 and outer cladding 930 have indices of refraction lower than that of the inner core 910, and the outer cladding 930 typically has a lower index of refraction than that of inner cladding 920 (although other refractive index profiles are possible). Inner core 910 may propagate only a single mode, and the OCT light may propagate to the probe handpiece through inner core 910. Intermediate cladding 920 is concentrically arranged around inner core 910, and may be capable of propagating multiple modes. The endoillumination light preferably propagates through intermediate cladding 920. Outer cladding 930 confines the endoillumination light in outer core 920. Thus, inner core 910 and intermediate cladding 920 each function as a "waveguide" for a specific wavelength, mode, or type of light. Additional cladding layers may be incorporated to enable additional parallel waveguides for light propagation. In an embodiment, other types of fiber, e.g., air-clad or photonic crystal fibers, may be utilized in a similar manner as that described above for double-clad fiber 900.

Figure 10A:
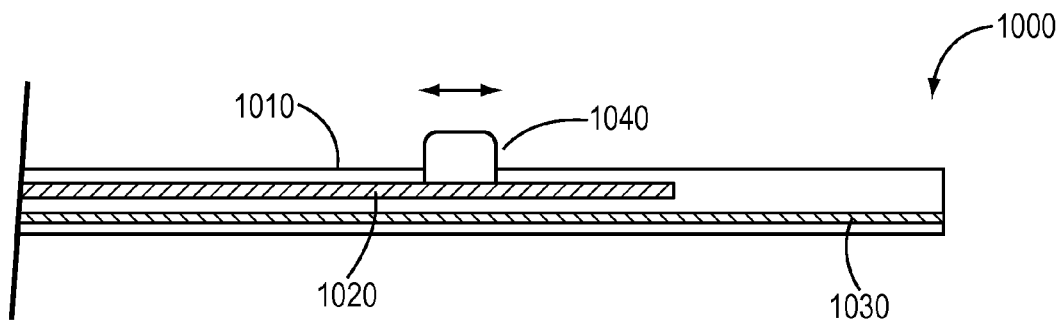
FIGS. 10A-10C depict three probe tip designs for probe systems in accordance with various embodiments of the invention.
Figure 10B:
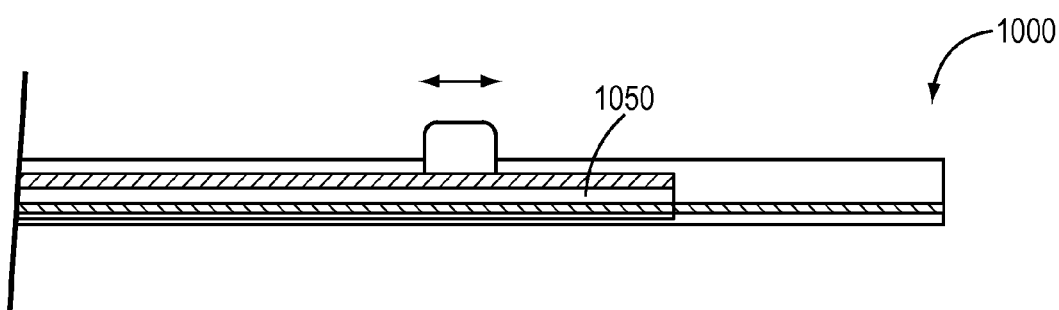
Figure 10C:
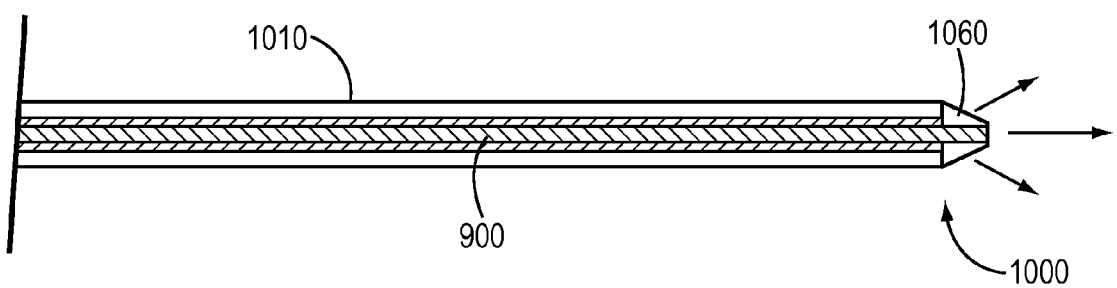

FIGS. 10A-10C depict three different fiber and lens configurations according to various embodiments of the invention. In the configuration shown in FIG. 10A, probe tip 1000 features an outer needle 1010 containing two fibers 1020, 1030. Fiber 1020 may be a multi-mode fiber for propagating endoillumination light to the end of probe tip 1000. As depicted, fiber 1020 is housed within an inner needle that is itself nested within outer needle 1010. The end of fiber 1020 is preferably recessed from the end of probe tip 1000 in order to enable wider dispersion from the fiber 1020 (and eventually from probe tip 1000), resulting in a larger illuminating spot diameter for endoillumination. The spot size may be adjusted through use of a slide lever 1040 that is mechanically coupled to fiber 1020 (or the inner needle housing fiber 1020). Movement of slide lever 1040 along the longitudinal axis of outer needle 1010 adjusts the distance between the end of fiber 1020 and the end of probe tip 1000, resulting in different illumination spot sizes. The configuration shown in FIG. 10B is similar to that of FIG. 10A, except both fibers 1020, 1030 are housed within an inner needle 1050. Here, fiber 1020 is fixedly mounted within inner needle 1050 such that it moves with inner needle 1050 when slide lever 1040 is repositioned. Fiber 1030 preferably threads through inner needle 1050 but is attached to outer needle 1010 such that it does not move when slide lever 1040 is moved.

In the configuration shown in FIG. 10C, fibers 1020, 1030 are replaced by double-clad fiber 900. In an embodiment, the light in the inner core of double-clad fiber 900 (e.g., light for OCT) passes through double-clad fiber 900 and exits probe tip 1000 through an opening in lens 1060. The light in the outer core of double-clad fiber 900 (e.g., light for endoillumination) passes through double-clad fiber 900 and exits probe tip 1000 through lens 1060, which disperses the light, enlarging the resulting spot size for, e.g., endoillumination. In an alternative embodiment, lens 1060 collimates or focuses the light from the inner core of double-clad fiber 900. Lens 1060 may be a GRIN lens or a Fresnel lens.

Figure 11A:
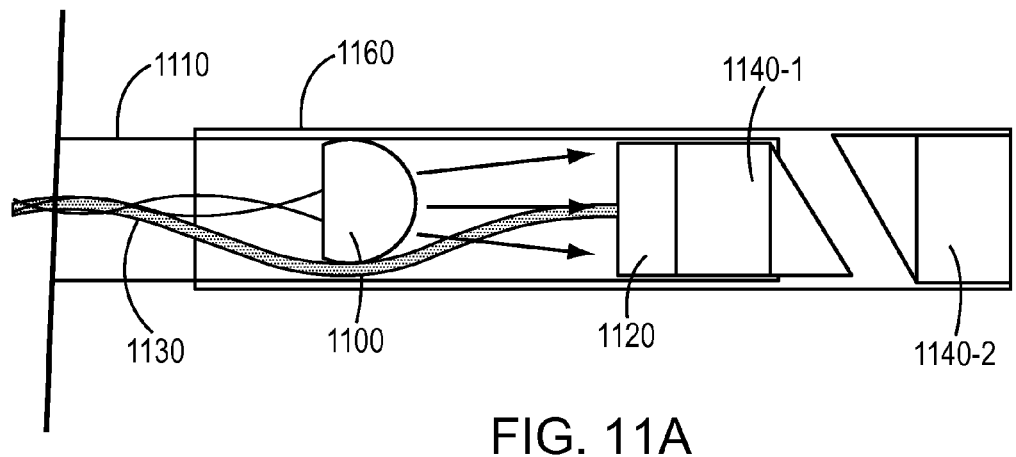
FIGS. 11A, 11B, and 11C schematically depict methods of coupling light from a light source into probe tips in accordance with various embodiments of the invention.
Figure 11B:
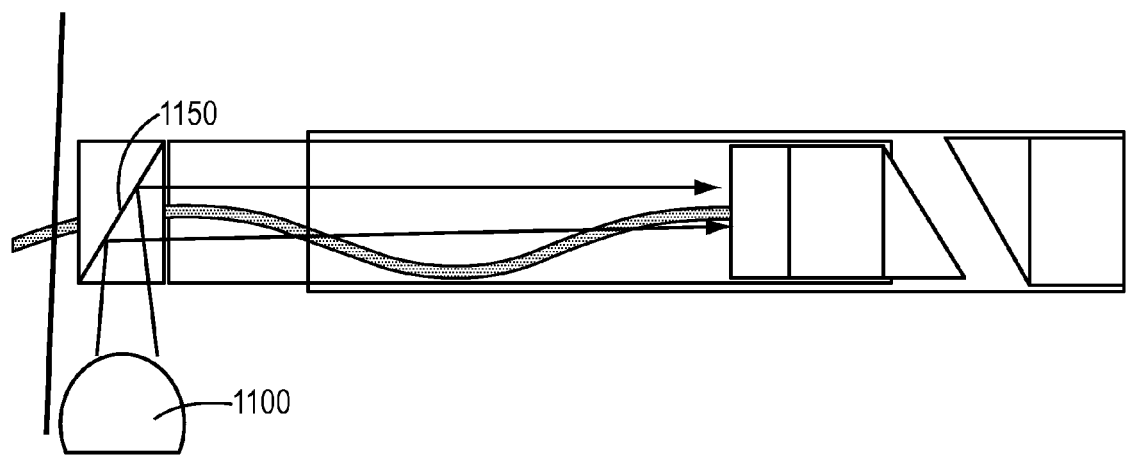
Figure 11C:
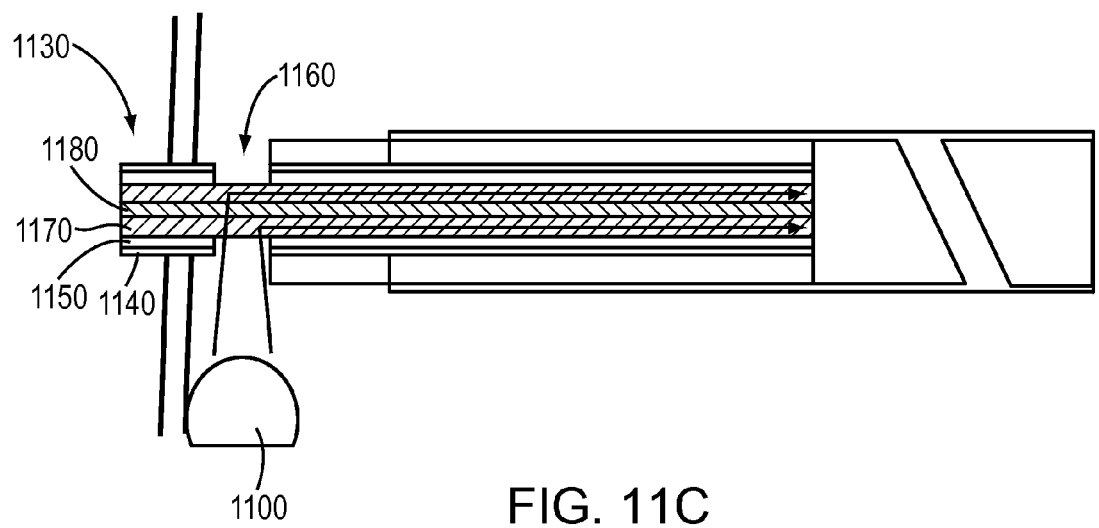

Referring to FIGS. 11A, 11B, and 11C, in various embodiments, a white-light source 1100 for endoillumination (e.g., an LED) is integrated into the probe handpiece or tip. The white-light source 1100 may be mounted (e.g., press-fit or with epoxy) within the inner needle 1110 or integrated into a glass ferrule 1120 that holds the inner fiber 1130 in place. Light from white-light source 1100 shines through the lens assembly (i.e., inner lens 1140-1 and outer lens 1140-2) to provide endoillumination functionality. Embodiments that incorporate a FORJ (as described above) may also include an electrical slip ring or rotary joint for the power connections to white-light source 1100. Alternately, light from white-light source 1100 may be coupled into the light path via one or more optical components 1150 (e.g., a prism and/or mirror) or via fiber coupling (e.g. fused fibers or WDM integrated into the handpiece). In one embodiment, a prism or mirror with a hole to permit passage of the probe fiber 1130 is mounted stationary behind the rotating needle assembly and is used to focus or couple white light from white-light source 1100 into the needle assembly, as shown in FIG. 11B. In another embodiment shown in FIG. 11C, inner fiber 1130 is double-clad fiber with its outer jacket 1140 and outer cladding layer 1150 removed in portion 1160 to allow for light from white-light source 1100 to be coupled into the intermediate cladding layer 1170 (which surrounds core 1180).

In many embodiments, it is desirable to have different beam spot sizes for different probe functionalities. For example, it may be desirable to minimize the spot size of the OCT beam for purposes of resolution, while it may be desirable to maximize the spot size of the endoillumination beam (and, therefore, the area under illumination). This may be accomplished in probe systems incorporating multiple fibers, where each light path may have its own fiber diameter or lensing and/or collimating system at the distal end. In a single-fiber configuration, this may be accomplished by providing a mechanism for adjusting the distance between lenses 1140-1, 1140-2. In one embodiment, the two nested needle assemblies are moved linearly relative to each other (e.g., the outer needle 1160 moving towards the distal end, or the inner needle 1110 moving towards the proximal end, or a combination of both) by a slide, lever, or twist mechanism manipulated by the user. Similarly, this may also be used to adjust the spot size of the treatment laser.

As previously mentioned, a variety of scanning patterns may be achieved by counter-rotating the nested lens assemblies and varying their speeds relative to each other. This may be particularly beneficial during endoillumination in a single-fiber probe, as the total area illuminated may be adjusted from a single spot (achieved with no rotation of the lens assemblies) to a wide circular region with a radius adjustable by the operator (and achieved by rapidly scanning the needle tips to produce a volumetric circular scan). Similarly, a linear illumination pattern (similar to a slit-lamp) may be achieved by rapidly scanning both needles at approximately the same speed. These methods may be used in conjunction with, or as an alternative to, the aforementioned method of adjusting the distance between lenses 1140-1, 1140-2. Alternatively, the distance between the lens 1140-1 and ferrule (e.g., ferrule 1120) may be adjusted to alter the focusing properties of the lens configuration. Likewise, the treatment laser may be scanned in a variety of patterns; for example, the spot size may be increased slightly by counter-rotating the lenses 1140-1, 1140-2 such that a small circular or linear pattern is scanned with a radius or length determined by the user.

Figure 12:
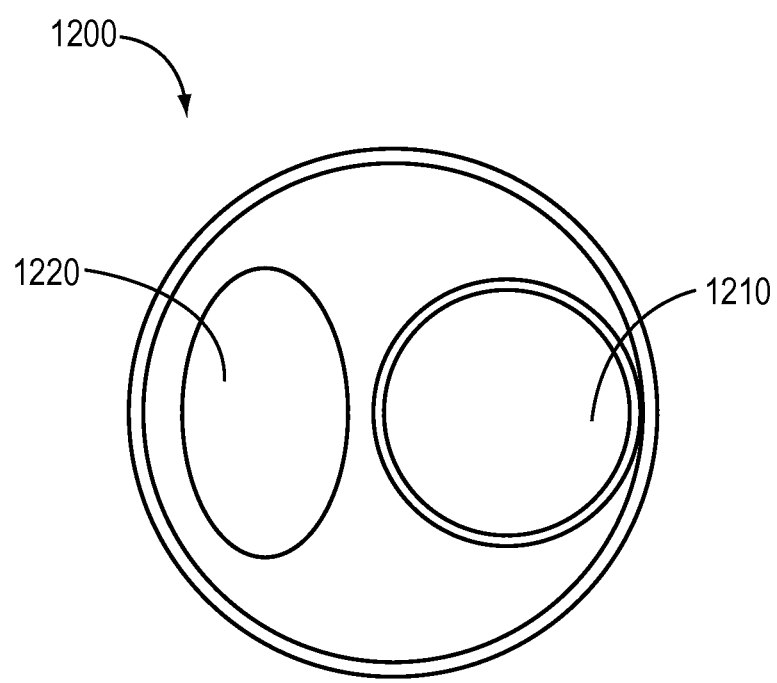
FIG. 12 is a schematic cross-section of a probe tip in accordance with various embodiments of the invention.

Some embodiments of the present invention combine any of the above-described optical functionalities with additional non-optical diagnostic and/or therapeutic functionality. FIG. 12 depicts a probe tip 1200 incorporating both the previously described optical lens assembly 1210 and an ultrasonic transducer 1220. The transducer 1220 may be made from a piezoelectric ceramic material that mechanically deforms a diaphragm and produces high-frequency sound waves when driven by a high-frequency AC signal, e.g., a 2 MHz sinusoid. Detection of the reflected sound waves enables sonographic image reconstruction that may be used, for example, to detect retinal tumors. Doppler and pulsed-width Doppler sonographic techniques may additionally be applied to detect and measure blood flow characteristics in blood vessels. A variety of transducer shapes, including round, oval, curved, etc., may be incorporated depending on the application. The fiber and/or lens assembly may be located adjacent to the transducer or the transducer may have a hole to accommodate the fiber and/or lens assembly. These geometries may be designed to maximize signal quality or minimize the dimensions of probe tip 1200.

Figure 13:
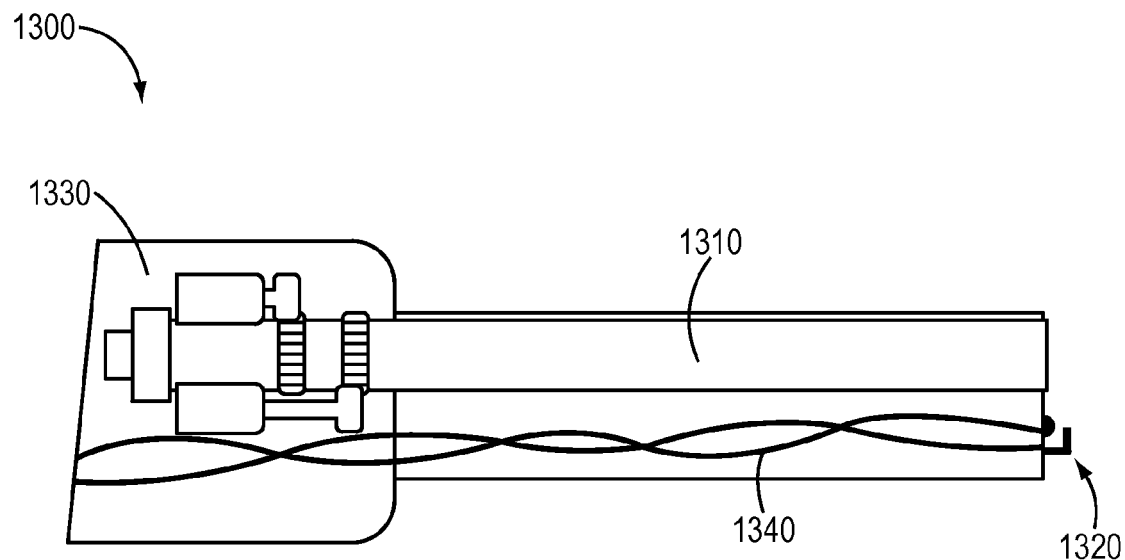
FIGS. 13 and 14 are schematic cross-sections of probes incorporating various functionalities in accordance with various embodiments of the invention.

Referring to FIG. 13, embodiments of the invention may also incorporate an electrocautery or ablation probe that may be used to burn tissue and/or cauterize blood vessels. Probe tip 1300 incorporates OCT functionality via optical assembly 1310, as well as electroautery functionality via high-frequency alternating currents passed through electrodes 1320 on probe tip 1300. The current is conducted through handpiece 1330 through conductive leads 1340 connected to electrodes 1320. This may be especially useful for imaging and treating diseased cartilage as in the case of osteoarthritis or ligament repairs for knee and shoulder surgery. A variety of electrocautery or ablation probe-tip geometries may be interchanged to suit a particular application.

Figure 14:
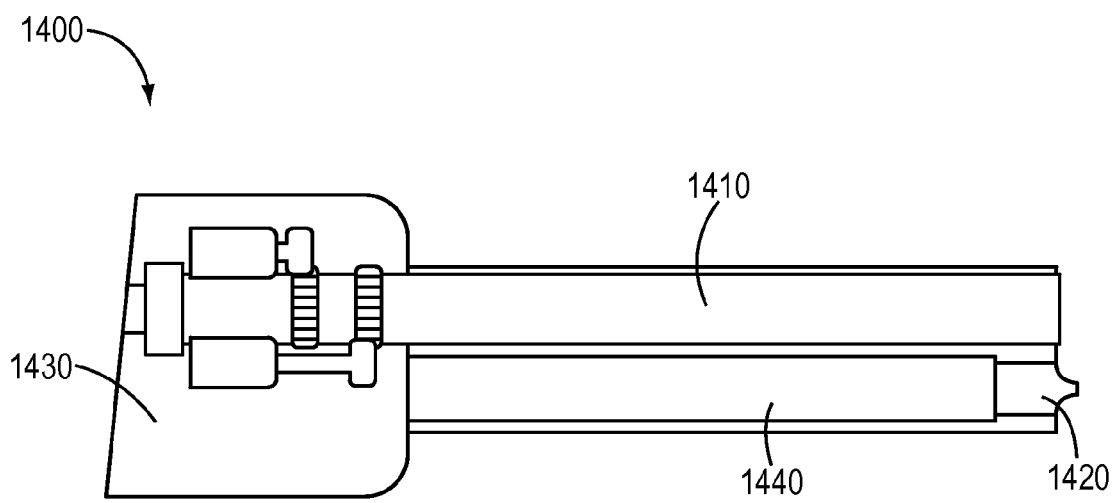

Referring to FIG. 14, a probe tip 1400 incorporates OCT functionality via optical assembly 1410, as well as a cryosurgical probe. A nozzle 1420 is designed to facilitate application of a pressurized fluid (e.g., a gas or liquid such as $CO_2$, $N_2O$, and/or liquid $N_2$) and is located within the probe tip 1400 adjacent to one of the previously described optical lens assemblies 1410. Nozzle 1420 connects to a source line 1440 that feeds through handpiece 1430 to an internal or external supply of the pressurized fluid. The cryosurgical probe may be useful when complemented with the OCT imaging functionality in a dermatological application or any application treating epithelial cells such as gynecological procedures (e.g., for treating potential human papillomavirus infections or cancer of the cervix). For example, the OCT probe may be used for diagnostic purposes (e.g., identifying a suspect tissue sample such as benign or malignant epithelial or dermal tissue growths) while the cryosurgical function may be used for treatment purposes (e.g., destroying the suspect tissue sample or skin lesion).

The nozzle 1420 may be angled to direct treatment to the exact location of the OCT beam. In one embodiment, the pressurized fluid is sourced from an external refillable tank with sufficient capacity for multiple treatments; in another embodiment, the gas or liquid is supplied from a small, single-use disposable pressure canister included in the probe handpiece 1430 that also houses optical assembly 1410.

One embodiment of the probe utilizes nozzle 1420 as a means of delivering fluid from the probe tip 1400 to, for example, irrigate the site, wash away blood or other fluid, or deliver a drug (such as an anti-inflammatory medication, e.g., an NSAID, for the spine) or a diagnostic stain (such as one or more dyes for lymph node evaluation). The fluid may be contained within a vessel located within the handpiece 1430 or it may be contained outside of the handpiece 1430 and provided through, e.g., a length of flexible tubing. A mechanical or electrical pumping mechanism may be used to provide sufficient pressure to pump fluid out of the distal end of the probe. The probe tip may likewise incorporate an aspirator to provide suction for the removal of fluid, tissue, and/or particles.

The pumping mechanism may be used as an irrigator to remove fluid and other debris from the OCT lens in order to ensure optimal imaging capabilities. A complementary or alternative means of ensuring the OCT lens is not partially or completely occluded is by mounting a mechanical wiper on the tip of the probe that cleans the surface of the lens when the wiper is rotated across the face of the lens. In one embodiment, the wiper is driven by a linkage rod or axle installed parallel to the needle assembly and that rotates the wiper across the lens surface when activated (e.g., manually or via the probe motor assembly in response to the user providing an instruction by, e.g., pressing a button on the handpiece).

A variety of tools for mechanical manipulation of tissue may also be incorporated into the probe tip adjacent to the distal end of the optical lens assembly 1410. For example, an optical probe used by a retinal surgeon may also incorporate a scalpel blade (in a variety of sizes and configurations) or a set of microforceps to aid the surgeon in performing a particular surgical procedure. As a further example, orthopedic procedures utilize a similar endoscopic approach as ophthalmic procedures, but with a different selection of tools and on a larger size scale. The increased size and varied tool selection provides several additional opportunities to combine the OCT probe with other mechanical probes or instruments not explicitly described herein.

Proximity Detection

In various embodiments, the probe systems described herein may be utilized with a trocar cannula system. A trocar cannula system is typically a small cannula that penetrates the skin tissue just enough to serve as the portal through which operative instrumentation (e.g., a laparoscope) is passed. Insertion of the cannula is aided by a pointed trocar device residing inside the cannula during, for example, a sclerotomy for the eye or insertion into the knee. The surgically placed cannulas allow the surgeon to have several open orifices from multiple cannulas through which to insert tools or probes inside the body. Trocars (or contact lens systems with multiple holes for instrument placements) may be used to place flexible, thin-walled cannulas, for example, resulting in 23-gauge sclerotomies. The trocar cannulas are used to maintain alignment between the offset conjunctival incision and the sclerotomy, facilitate finding the small incisions when inserting tools, and for giving closed-loop feedback to the Z-axis movement and, possibly, the angular movement of the probe. Optimal placement of the probe during endoillumination and OCT modes are typically approximately 10 mm and 3 mm, respectively, from tissue such as a retina. While a user is utilizing the OCT functionality of the probe, inadvertently activating the endoillumination functionality while too close to various tissues may be problematic. Therefore, in various embodiments, the probe system provides specific feedback proportional to the in-and-out movement of the probe within a cannula or axial displacement of the probe relative to a cannula.

In a preferred embodiment, information from the OCT signal itself may be used to determine the distance from the probe tip to the tissue of interest with or without the use of a trocar cannula system. Because the processed OCT signal includes a reflectance profile of the tissue of interest, the first measured reflection (excluding reflections at the lens interfaces) may be used to accurately determine distance to the surface of the tissue of interest. Furthermore, biometric measurements may be derived in the same manner by detecting reflections from multiple features (e.g. tissue and/or fluid interfaces, biological structures, etc.) and calculating the distance between these features.

Figure 15:
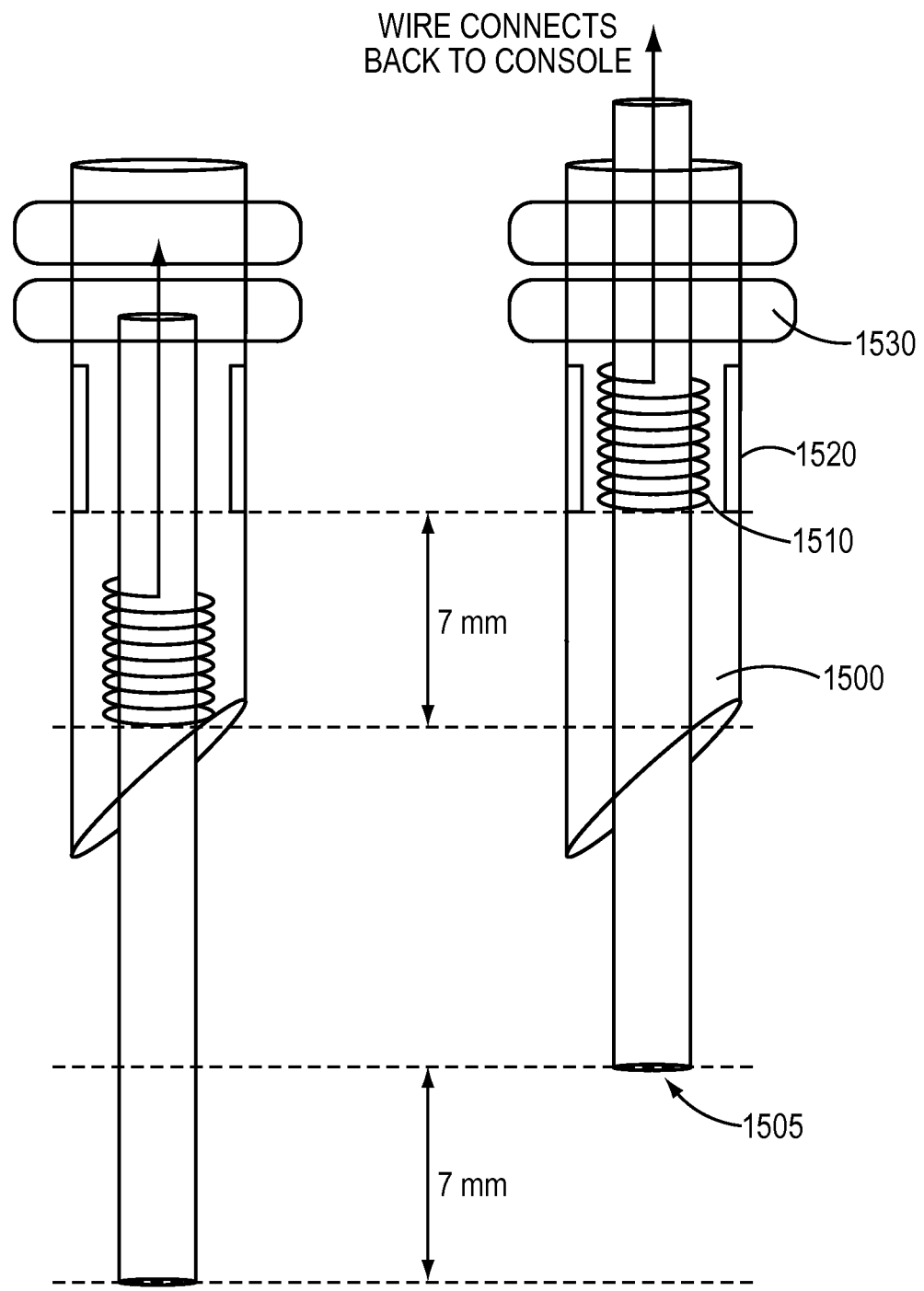
FIG. 15 is a schematic diagram of a trocar cannula system utilized with probes in accordance with various embodiments of the invention.

Referring to FIG. 15, in various embodiments, a fiduciary cannula containing magnetic material 1500 is inserted through the tissue of interest. This cannula is used to provide feedback to the console indicating the probe tip's z-axis position above an anatomical feature, e.g., a retina. In this embodiment, the probe 1505 contains a coil 1510 in the needle assembly and is inserted into the fiduciary cannula. The cannula contains magnets or magnetized elements that are aligned such that, when the probe 1505 is inserted into the cannula, the magnetic field induces a current in the coil 1510 that is measured and from which the direction of movement, rate of movement, and position of probe is derived. The coil 1510 may be connected to additional electronics (such as an amplifier to assist in measuring and conditioning the signal) that are located either in the handheld probe 1505 or in the console. In some embodiments, the endoillumination functionality is disabled or intensity-limited when the tip of probe 1505 is located within a specific range of the tissue. For example, the system may be implemented to require a surgeon using the probe at approximately 3 mm from a retina to bring the probe to approximately 10 mm from the retina before endoillumination may be enabled or increased in intensity. (FIG. 15 depicts such a 7-mm range of travel.) In this manner, the surgeon is prevented from shining too much light on the retina in close proximity thereto (as phototoxicity to the retina depends on intensity, distance of light from the retina and wavelengths of light). Furthermore, this feedback system may also implement selective wavelength filtering, where more dangerous (e.g., phototoxic) wavelengths are reduced in intensity or disabled at close distances (e.g., 3 mm) but increased as distance increases. Another embodiment implements magnetic-field sensing using a Hall-effect sensor instead of the coil; yet another embodiment incorporates the sensing element (e.g., coil or Hall-effect sensor) in the cannula and incorporates the magnet in the probe needles (alternately, the needles are magnetized).

FIG. 15 depicts a cannula 1500 made of a biocompatible material (e.g., a biocompatible plastic or polymer) with one or more magnets 1520 mounted on or within the cannula 1500. Plugs 1530 hold the cannula 1500 in place once it is inserted. The magnet 1520 is positioned such that it is aligned with the coil 1510 on the probe 1505 when the probe 1505 is inserted into the cannula 1500. Movement of the coil 1510 past the magnet 1520 induces a current in the coil 1510 that may be measured and from which the direction and rate of movement and position of the probe 1505 may be derived. The control firmware or software may respond according to the movement or position of the probe 1505. For example, the intensity of endoillumination may be increased automatically as distance increases. This may also be applied to therapeutic lasers, by creating a safety mechanism to prevent inadvertent discharge of the probe. In other embodiments, the relative placement of the magnet 1520 and coil 1510 is reversed, i.e., the coil 1510 is in or on the cannula and the magnet(s) 1520 are on the probe 1505.

In another embodiment, the distance of the probe tip to the tissue surface (e.g., a retina) is determined by the magnitude of reflected light captured by the lens of the probe, where the amount of light captured is inversely proportional to the distance to the surface of interest (e.g., the retina). Another embodiment incorporates an accelerometer and/or gyroscope in the handpiece to determine position and/or orientation. For example, the accelerometer may be activated upon insertion into the cannula, and the relative position of the probe may be determined by integrating the measured acceleration. Another embodiment incorporates evenly-spaced indicators inside the cannula (or alternately along the probe needle) that may be detected (e.g., with a photoreflector or optical encoder mounted in the probe needle or, alternately, in the cannula) and provide a measure of probe tip displacement when the probe is moved in and out of the cannula.

OCT Functionality

In various embodiments, the probe systems described herein may be utilized to take and process A-scans, B-scans, and/or C-scans of specific tissue, e.g., a retina. Applications of this technique may include cataract surgery, choroidal neovascularization, localized beta radiation, macular translocation, membrane peels, ocular trauma, retinal detachments, retinal transplantation, subretinal hemorrhage (or other fluid), surgical management of intraocular foreign bodies, vitrectomy, anterior segment reconstruction after ocular trauma, diagnosis and initial management of penetrating eye injuries, management of the opaque media eye with no light perception, pharmacologic manipulation of the vitreous during pars plana vitrectomy, primary surgical management of penetrating eye injuries, surgical management of ocular rupture, and surgical management of the choroid in ocular trauma.

Figure 16:
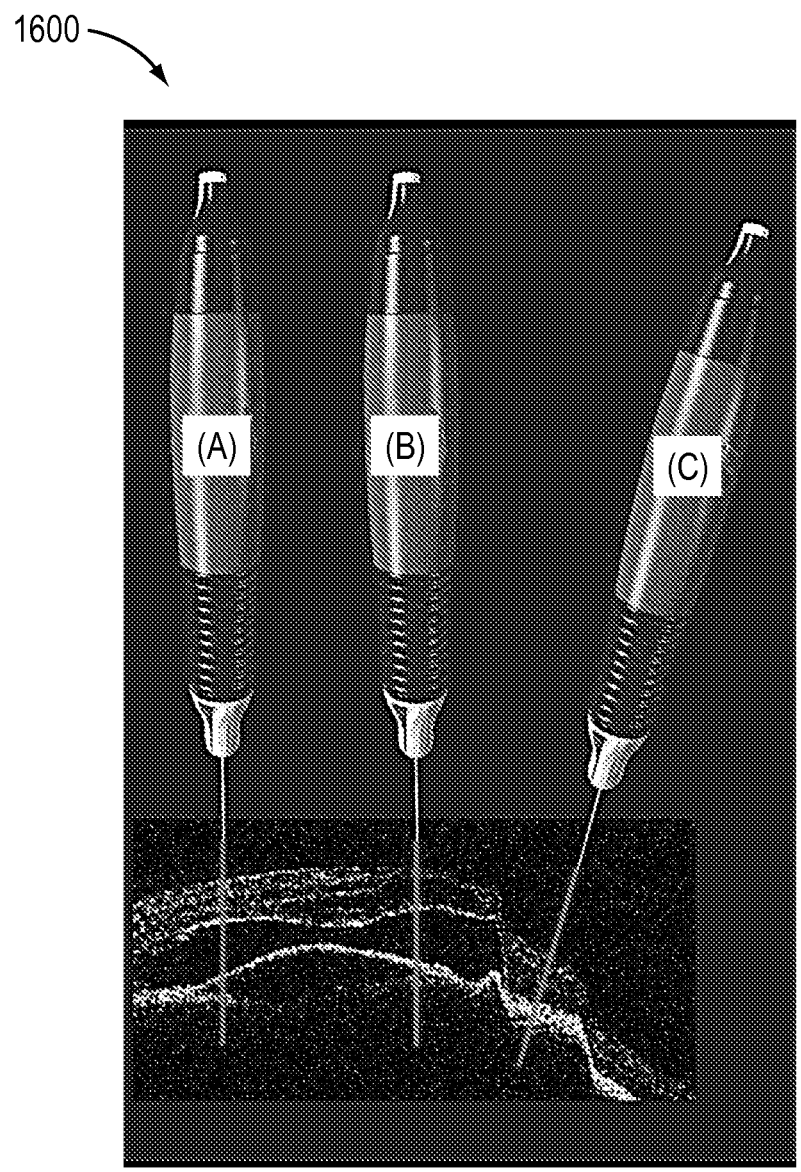
FIGS. 16 and 17 depict various scanning positions for probes in accordance with various embodiments of the invention.

In one embodiment, the probe is used to identify and/or locate, for example, a collection of subretinal fluid underlying an area of the retina. FIG. 16 illustrates the use of a probe 1600 to indicate the presence of fluid under the pigment epithelial detachment. Three locations of probe 1600 are indicated in FIG. 16, labeled (A), (B), and (C). Each probe position captures a different A-scan profile of the tissue structure, indicating fluid presence and providing spatial measurements, for example, to calculate an estimate of volume. Further, the A-scan measurements of probe 1600 may determine the consistency (and flow if present, via Doppler) of the fluid and alert to serous, watery, or bloody fluid, as in the depicted positions (A) and (B). Or, for example, the probe 1600 may measure no fluid, indicating a healthy retina, as in the depicted position (C). The probe 1600 may be used in a similar fashion in other medical applications such as orthopedics, for example, to quantify the grade of chondromalacia in the articular cartilage of the knee or in neurosurgery, for example, to distinguish grey matter from white matter. In this fashion, probe 1600 may act like a "dipstick," enabling a surgeon to perform a simple but standardized diagnostic check on a patient, such as measuring the fluid under the retina or the macular hole in the middle of a procedure in order to gauge the clinical severity of the case.

In addition to sensing the presence of fluid, the probe 1600 may be utilized to quantify or measure the amount of fluid under the retina. Probe 1600 may also extrapolate a bleb, for example, using a five-point inspection around the inside rim (or other types of areas). Additionally, probe 1600 may be moved over a bleb in an inward spiral, in order to determine its volume. The volume may be measured by integrating the calculated height or thickness of the bleb as the light beam is swept over the entire surface of the bleb. Probe 1600 may be utilized to measure the content of a fluid (e.g., serous exudate, clear fluid, or bright red blood, an indication of possible active bleeding) in a biological sample.

Other applications of probe 1600 include measuring retinal thickness as an indicator for Anti-VEGF or other results from drug delivery, or even the amount of polymer and/or drug on the end of a drug delivery device. Probe 1600 may be utilized to measure the patency or amount of biological debris of a drug pump cannula or glaucoma drainage device. Furthermore, probe 1600 may be utilized in anterior procedures such as measurement of the angle of the ciliary body or the thickness of a cataract or the position of a haptic lens, or the placement of haptics or the integrity of the capsular bag.

Figure 17:
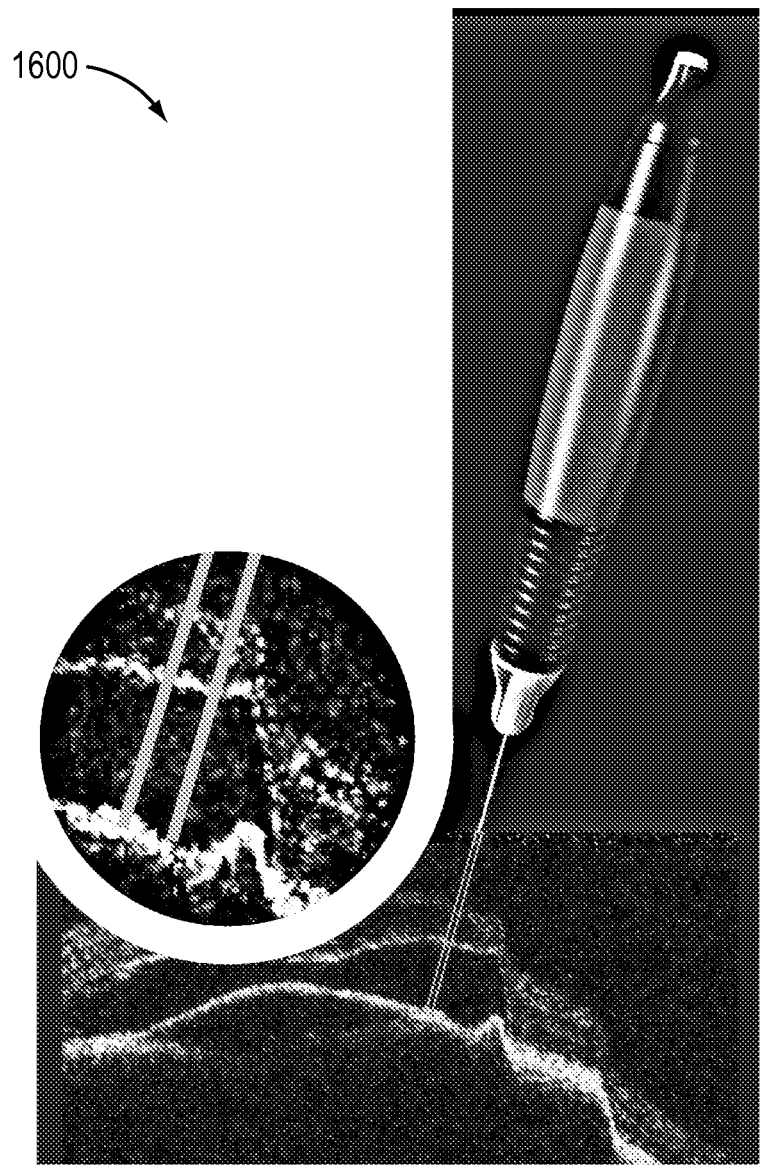

Referring to FIG. 17, in some embodiments of the present invention, probe 1600 incorporates multiple OCT fibers, enabling multiple simultaneous A-scans on a single sample. The multiple OCT fibers may lie alongside each other in probe 1600, or light from two different OCT light sources may be coupled into a single double-clad fiber. The OCT fibers may protrude slightly from the probe tip, and may be oriented in different directions (e.g., 45° or 90° relative to each other) to enable measurements of areas difficult to access. In an embodiment, two OCT fibers are angled relative to each other (e.g., perpendicular to each other), and the handpiece of probe 1600 may be rotated up to 90° in order to scan the area of interest, for example, for image reconstruction. The propagating light may be switched between the different fibers via a variety of optical switching means, or multiple back-end consoles may be used to process multiple A-scan data streams at once. In an embodiment, any of the multiple OCT fibers may be utilized to perform B-scans and/or C-scans, as well as A-scans.

Figure 18:
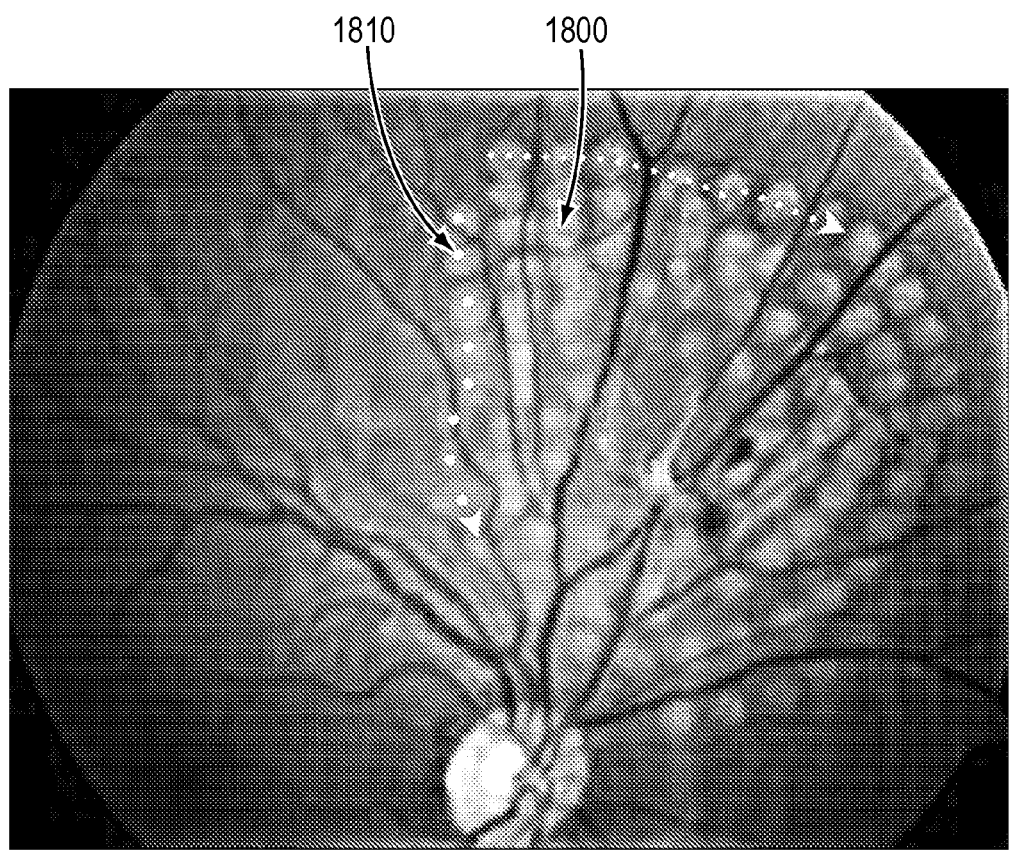
FIG. 18 depicts an exemplary scanning application for probes in accordance with various embodiments of the invention.

In an embodiment, probe 1600 is used to measure the effectiveness of a laser-treatment burn. This includes a laser burn (i.e., a photocoagulation) from a therapeutic laser treating chorioretinal lesions during the course of a vitrectomy procedure, for example (in cases of wet AMD or diabetic retinopathy). In this method, during or after the application of the therapeutic laser, the surgeon captures an A-scan or series of A-scans in order to monitor the progress of the burn or to quantify the quality of the retina burn. FIG. 18 depicts the rasterized pattern 1800 of a Pascal therapeutic burn on a retina, as well as an approximate path 1810 of OCT A-scan readings performed by a surgeon with probe 1600 (or probe 1700). Each "stop" along path 1810 corresponds to the approximate center of each of the burns in pattern 1800. At each stop, probe 1600 performs A-scans to take particular measurements (including counting of underlying layers, evaluating the fluid in and out of blood vessels, and/or contrast). The measurements may be compared against databases or tabulated values pertaining to the retina layers, thickness, etc. in order to predict the necessity of performing a replacement burn or the need for other additional treatment. Each of the set of A-scan measurements may be activated via a foot pedal or via controls (e.g., tactile buttons, resistive or capacitive sensing, or gesture-based control) on the handpiece of probe 1600. Probe 1600 may be activated continuously (and therefore uses software to recognize when it is over a burn) or a clinician may activate the probe when it is centered over each clinical target (such as an individual burn). During the burn itself, the OCT functionality of probe 1600 may also be activated at the same time as the therapeutic laser to provide real-time feedback on the status and quality of the burn, thereby enabling adaptive control of the therapeutic laser.

Probe Gestures

Figure 19:
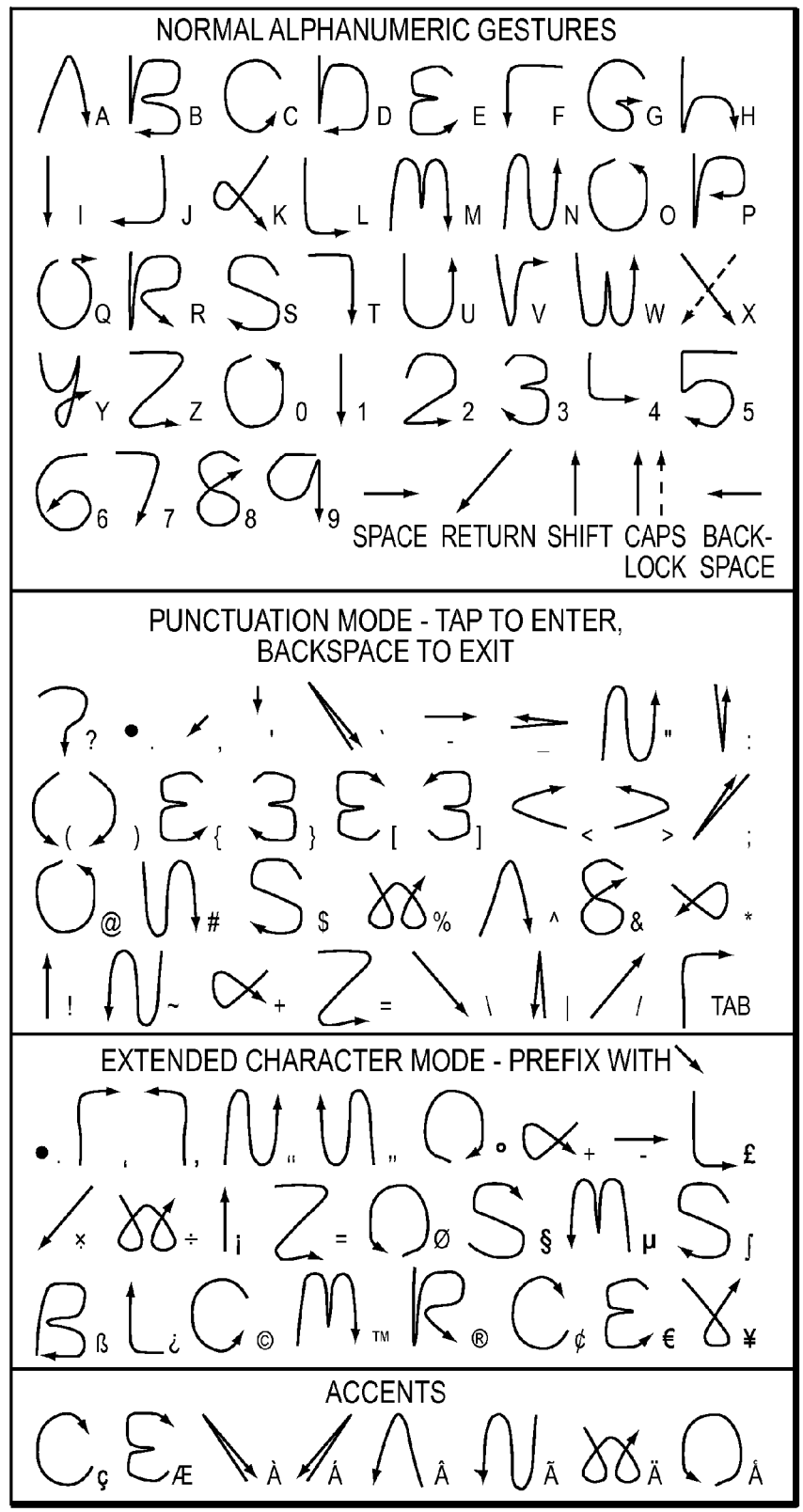
FIG. 19 depicts an exemplary set of gestural commands for probes in accordance with various embodiments of the invention.

In various embodiments, the probe and/or control console processes the position and orientation of any of the above-described probes. This may be accomplished in a variety of ways including, but not limited to, the use of a gyroscope within the probe handpiece to sense orientation (e.g., three-axis roll, pitch, yaw), an accelerometer to sense motion along particular axes, or a camera- or vision-based tracking system. In one particular embodiment of such a tracking system, the camera detects markers located on the probe (e.g., infrared LEDs oriented in a particular configuration) and calculates position and orientation of the probe based on the position of the light points as captured by the camera (e.g., through trigonometric functions). In another embodiment, the camera is a "time-of-flight" camera that captures a distance profile (e.g., by measuring the amount of time it takes an infrared pulse located at the camera position to reflect off different regions on the surface of interest and return to the camera), and the resulting information is used to estimate the position and orientation of the probe. Using these sense capabilities the surgeon is able to control functions of the probe through gestures made while holding the probe. FIG. 19 depicts exemplary gesture-based alphanumeric input strokes that may be utilized to control various functions of the probe. In one embodiment, the surgeon uses the aiming beam to "paint" letters or symbols that are recognized by the console as command inputs. For example, an "R" gesture may start the "Recording" on the OCT monitor. Other gestures may correspond to commands for laser type, brightness, OCT wavelength, or other variables to aid surgery.

Other gestures, such as rotating the probe clockwise or counter-clockwise, may be sensed by the sensor and used to control functionality (e.g., to adjust endoillumination intensity). For example, the surgeon may rotate the probe (A) left 90°, (B) right >45° and (C) left >90° to communicate a specific command to the console. Audio feedback from the console such as voice confirmation or audible tones may be utilized to confirm the surgeon's intention.

The probe may also be used to detect distance from the tip of the probe to the surface of the tissue being imaged to, for example, maintain the ideal working distance or warn the surgeon if the probe is too close to the surface (e.g., the retina). While this may be accomplished using a variety of methods (e.g., sensors), it may readily be achieved using the reflected OCT signal (measured or digitized by the OCT console hardware) to identify the reflection off the surface of interest and measure the distance to that surface.

Further, an accelerometer (or another shock or vibration sensor such as a piezoelectric element) may detect subtle "finger taps" or patterns of taps on the handpiece as a means of controlling functionality. In addition, the probe may include other activation or control methods, such as tactile switches, capacitive touch sensing, and/or piezoresistive sensing (either in a binary "on-off" configuration or in a continuous analog configuration whereby the amount of force applied to the piezoresistive material may be quantified, for example to increase intensity with harder squeezing). Any of these gesture- or tactile-based control methods may be implemented any of the probes described herein.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An imaging method, the method comprising:
providing a handpiece having (a) a probe tip insertable into human or animal tissue and disposed at an end thereof, and connected thereto, (b) an optical coherence tomography (OCT) probe and (c) a second probe, such that a functionality of the OCT probe and a second functionality associated with the second probe are provided at the probe tip;
disposing the probe tip adjacent to or into an ocular tissue;
measuring, with the OCT probe, at least one of a feature size or a quantifiable characteristic of a structure in the ocular tissue for biometry analysis; and
performing the second functionality on the articular cartilage tissue,
wherein the functionality of the OCT probe is provided by a first one of a plurality of distinct parallel waveguides provided within a single optical fiber disposed within the probe tip and the second functionality is provided by a second one of the plurality of distinct parallel waveguides within the single optical fiber.

2. The method of claim 1, wherein the probe tip is disposed into the tissue via a cannulated incision.

3. The method of claim 1, wherein the probe tip is disposed into the tissue via an open incision or an orifice.

4. The method of claim 1, wherein the second probe being selected from the group consisting of: an endoillumination probe, a laser therapy probe, an ultrasound imaging probe, an electrocautery probe, an RF ablation probe, a cryosurgical probe, an irrigator, and a mechanical probe.

5. The method of claim 1, wherein at least one of a feature size or a quantifiable characteristic of a lens capsule is measured with the OCT probe.

6. The method of claim 1, wherein at least one of a feature size or a quantifiable characteristic of a retina is measured with the OCT probe.

7. The method of claim 1, wherein measuring a feature size or quantifiable characteristic comprises quantifying quality of a treatment burn on a retina.

8. The method of claim 1, wherein the feature size or quantifiable characteristic comprises at least one of a corneal angle or a corneal thickness.

9. The method of claim 1, wherein the feature size or quantifiable characteristic comprises at least one of a thickness, an integrity, or an anatomical variation of a capsular bag.

10. The method of claim 1, the feature size or quantifiable characteristic comprises a thickness of a retina.

11. The method of claim 1, wherein measuring a feature size or quantifiable characteristic comprises measuring a volume of an intra-ocular fluid.

12. An imaging method, the method comprising:
providing a handpiece having (a) a probe tip insertable into human or animal tissue and disposed at an end thereof, and connected thereto, (b) an optical coherence tomography (OCT) probe and (c) a second probe, such that a functionality of the OCT probe and a second functionality associated with the second probe are provided at the probe tip;
disposing the probe tip adjacent to or into articular cartilage tissue;
measuring, with the OCT probe, at least one of a feature size or a quantifiable characteristic of a structure in the articular cartilage tissue for biometry analysis; and
performing the second functionality on the articular cartilage tissue,
wherein the functionality of the OCT probe is provided by a first one of a plurality of distinct parallel waveguides provided within a single optical fiber disposed within the probe tip and the second functionality is provided by a second one of the plurality of distinct parallel waveguides within the single optical fiber.

13. The method of claim 12, wherein measuring a feature size or quantifiable characteristic comprises quantifying a grade of chondromalacia in the articular cartilage tissue.

14. The method of claim 11, wherein the intra-ocular fluid comprises subretinal fluid.

15. The method of claim 12, wherein the feature size or quantifiable characteristic comprises at least one of a thickness or a density of the articular cartilage tissue.

* * * * *

UNITED STATES PATENT AND TRADEMARK OFFICE
CERTIFICATE OF CORRECTION

PATENT NO. : 8,914,098 B2  
APPLICATION NO. : 12/718266  
DATED : December 16, 2014  
INVENTOR(S) : Jeffrey Brennan et al.

Page 1 of 2

It is certified that error appears in the above-identified patent and that said Letters Patent is hereby corrected as shown below:

In the Claims:

Column 23, line 40, Claim 1 should read:

1. An imaging method, the method comprising:
   providing a handpiece having (a) a probe tip insertable into human or animal tissue and disposed at an end thereof, and connected thereto, (b) an optical coherence tomography (OCT) probe and (c) a second probe, such that a functionality of the OCT probe and a second functionality associated with the second probe are provided at the probe tip;
   disposing the probe tip adjacent to or into articular cartilage tissue or ocular tissue;
   measuring, with the OCT probe, at least one of a feature size or a quantifiable characteristic of a structure in the tissue for biometry analysis; and
   performing the second functionality on the tissue,
   wherein the functionality of the OCT probe is provided by a first one of a plurality of distinct parallel waveguides provided within a single optical fiber disposed within the probe tip and the second functionality is provided by a second one of the plurality of distinct parallel waveguides within the single optical fiber.

Column 24, line 21, Claim 9 should read:

9. The method of claim 16, wherein measuring a feature size or quantifiable characteristic comprises quantifying a grade of chondromalacia in articular cartilage tissue.

Column 24, line 55, Claim 15 should read:

15. The method of claim 16, wherein the feature size or quantifiable characteristic comprises at least one of a thickness or a density of articular cartilage tissue.

Signed and Sealed this  
Seventeenth Day of March, 2015

Michelle K. Lee  
*Director of the United States Patent and Trademark Office*

CERTIFICATE OF CORRECTION (continued)
U.S. Pat. No. 8,914,098 B2

Column 24, line 58, Claim 16 should read:

16. An imaging method, the method comprising:
    providing a handpiece having (a) a probe tip insertable into human or animal tissue and disposed at an end thereof, and connected thereto, (b) an optical coherence tomography (OCT) probe and (c) a second probe, such that a functionality of the OCT probe and a second functionality associated with the second probe are provided at the probe tip;
    disposing the probe tip adjacent to or into ocular tissue or articular cartilage tissue;
    measuring, with the OCT probe, at least one of a feature size or a quantifiable characteristic of a structure in the tissue for biometry analysis; and
        performing the second functionality on the tissue,
    wherein the functionality of the OCT probe is provided by a first one of a plurality of distinct parallel waveguides provided within a single optical fiber disposed within the probe tip and the second functionality is provided by a second one of the plurality of distinct parallel waveguides within the single optical fiber.